US009012197B2

(12) United States Patent
Bayne et al.

(10) Patent No.: US 9,012,197 B2
(45) Date of Patent: *Apr. 21, 2015

(54) PRODUCTION OF HEMAGGLUTININ-NEURAMINIDASE PROTEIN IN MICROALGAE

(75) Inventors: Anne-Cécile V. Bayne, Ellicott City, MD (US); James Casey Lippmeier, Columbia, MD (US); Kirk Emil Apt, Ellicott City, MD (US); Xuan Guo, Suwanee, GA (US); Joyce A. Pritchard, Gainesville, GA (US)

(73) Assignees: Merial, Inc., Duluth, GA (US); Sanofi Vaccine Technologies, S.A.S. (FR)

( * ) Notice: Subject to any disclaimer, the term of this patent is extended or adjusted under 35 U.S.C. 154(b) by 88 days.

This patent is subject to a terminal disclaimer.

(21) Appl. No.: 12/980,320

(22) Filed: Dec. 28, 2010

(65) Prior Publication Data
US 2011/0195480 A1   Aug. 11, 2011

Related U.S. Application Data

(60) Provisional application No. 61/290,469, filed on Dec. 28, 2009.

(51) Int. Cl.
*C12N 9/26* (2006.01)
*C12N 9/14* (2006.01)
*C12N 1/12* (2006.01)
*C12P 21/06* (2006.01)
*C07H 21/04* (2006.01)
*C07K 1/00* (2006.01)
*C12N 7/00* (2006.01)
*C12N 15/82* (2006.01)
*C12N 9/24* (2006.01)

(52) U.S. Cl.
CPC ........... *C12Y 302/01018* (2013.01); *C12N 7/00* (2013.01); *C12N 15/8257* (2013.01); *C12N 2760/18151* (2013.01); *C12N 2760/18651* (2013.01); *C12N 9/2402* (2013.01)

(58) Field of Classification Search
USPC .................... 435/201, 195, 257.2, 91.1, 69.1; 536/23.1, 23.2; 530/350
See application file for complete search history.

(56) References Cited

U.S. PATENT DOCUMENTS

| 4,659,669 | A | 4/1987 | Kleid et al. |
| 4,752,473 | A | 6/1988 | Nayak et al. |
| 5,340,742 | A | 8/1994 | Barclay |
| 5,762,939 | A | 6/1998 | Smith et al. |
| 7,001,772 | B2 | 2/2006 | Roessler et al. |
| 7,029,872 | B2 | 4/2006 | Gerngross |
| 7,759,097 | B2 | 7/2010 | Ono et al. |
| 7,851,191 | B2 | 12/2010 | Roessler et al. |
| 7,888,123 | B2 | 2/2011 | Ono et al. |
| 2003/0166207 | A1 | 9/2003 | Roessler et al. |
| 2004/0171826 | A1 | 9/2004 | Hamilton |
| 2004/0230042 | A1 | 11/2004 | Hamilton |
| 2005/0112719 | A1 | 5/2005 | Roessler et al. |
| 2005/0287172 | A1 | 12/2005 | Yang et al. |
| 2006/0029604 | A1 | 2/2006 | Gerngross et al. |
| 2006/0040353 | A1 | 2/2006 | Davidson et al. |
| 2006/0257399 | A1 | 11/2006 | Gerngross et al. |
| 2006/0275904 | A1 | 12/2006 | Ono et al. |
| 2006/0286650 | A1 | 12/2006 | Ono et al. |
| 2007/0128222 | A1 | 6/2007 | Kovacs et al. |
| 2007/0270494 | A1 | 11/2007 | Metz et al. |
| 2010/0233760 | A1 | 9/2010 | Apt et al. |
| 2011/0086390 | A1 | 4/2011 | Roessler et al. |
| 2011/0162115 | A1 | 6/2011 | Guo et al. |
| 2011/0189228 | A1 | 8/2011 | Bayne et al. |

FOREIGN PATENT DOCUMENTS

| WO | WO 99/02695 | 1/1999 |
| WO | WO 2004/098533 A2 | 11/2004 |
| WO | WO 2009/009876 A1 | 1/2009 |
| WO | WO 2009/101160 A1 | 8/2009 |

OTHER PUBLICATIONS

Miller et al., Antigenic differences among Newcastle disease virus strains of different genotypes used in vaccine formulation affect viral shedding after virulent challenge. Vaccine, 2007, vol. 25: 7238-7246.*
Griesbeck et al., *Chlamydomonas reinhardtii*, A protein expression system for pharmaceutical and biotechnological proteins. Mol. Biotechnol., 2006, vol. 34: 213-223.*
Eichler-Stahlberg et al., Strategies to facilitate transgene expression in *Chlamydomonas reinhardtii*. Planta, 2009, vol. 229: 873-883.*
Bendsten et al., "Improved prediction of signal peptides: SignalP 3.0," *J Mol. Biol.* 340:783-795, Elsevier, England (2004).
Chou, K.-C. and Elrod, D.W., "Prediction of Membrane Protein Types and Subcellular Locations," *Proteins: Structure, Function and genetics* 34:137-153, Wiley-Liss, Inc., United States (1999).
D'Aoust, M.-C., et al., "Influenza virus-like particles produced by transient expression in *Nicotiana benthamiana* induce a protective immune response against a lethal viral challenge in mice," *Plant Biotechnol. J.*6930-940, Blackwell Publishing Ltd, England (2008).
D'Aoust, M.-C., et al., "The Production of hemagglutinin-based virus-like particles in plants: a rapid, efficient and safe response to pandemic influenza," *Plant Biotechnol. J.*:8:607-619, Blackwell Publishing Ltd, England (2010).
Emanuelsson, O., et al., "Locating proteins in the cell using TargetP, SignalP and related tools," *Nature Protocols* 2:953-971, Nature Publishing Group, England (2007).
Floss et al., "Production of vaccines and therapeutic antibodies for veterinary applications in transgenic plants: an overview," *Transgenic Res.* 16:315-332, Kluwer Academic Publishers, Netherlands (2007).
Fuhrmann et al., "Production of Antigens in *Chlamydomonas reinhardtii*: Green Microalgae as a Novel Source of Recombinant Proteins," *Methods in Molecular Medicine* 94:191-195, Humana Press Inc., Unites States, (2004).

(Continued)

*Primary Examiner* — Ganapathirama Raghu
(74) *Attorney, Agent, or Firm* — Judy Jarecki-Black; Ruoying Chen; Merial, Inc.

(57) ABSTRACT

The present invention is directed to recombinant microalgal cells and their use in production of heterologous hemagglutinin-neuraminidase (HN) polypeptides, as well as compositions and uses thereof.

12 Claims, 10 Drawing Sheets

(56) References Cited

OTHER PUBLICATIONS

Guo, X., et al. "Lemna (duckweed) expressed hemagglutinin from avian influenza H5N1 protects chickens against H5N1 high pathogenicity avian influenza virus challenge," *Abstracts of the 7th International Symposium on Avian Influenza*, Apr. 5-8, 2009, Athens, Georgia. p. 62. Publication date: Apr. 5, 2009.

Joensuu et al., "Transgenic plants for animal health: plant-made vaccine antigens for animal infectious disease control," *Phytochem Rev.* 7:553-577, Kluwer Academic Publishers, Netherlands (2008).

Nagy, É., et al., "Synthesis of Newcastle disease virus (NDV)-like envelopes in insect cells infected with a recombinant baculovirus expressing the haemagglutinin neuraminidase of NDV,"*J. Gen. Virol.* 72:753-756, The Society for General Microbiology, England (1991).

Nielsen, H. and Krough, A., "Prediction of signal peptides and signal anchors by a hidden Markov model," *Proc. Int. Conf. Intell. Syst. Mol. Biol.* 6:122-130, AAAI Press, United States.

Nielsen, H., et al., "Machine learning approaches for the prediction of signal peptides and other protein sorting signals," *Protein Engineering* 12(1):3-9,Oxford University Press, England (1999).

Prasad, V., et al., "Expression of biologically active Hemagglutinin-neuraminidase protein of *Peste des petits ruminants* virus in transgenic pigeonpea," *Plant Sci.* 166:199-205, Elsevier Ireland Ltd., Ireland (2004)

Sim, J.-S., et al., "Expression and Characterization of Synthetic Heat-Labile Enterotoxin B Subunit and Hemagglutinin-Neuraminidase-Neutralizing Epitope Fusion Protein in *Escherichia coli* and Tobacco Chloroplasts," *Plant Mol. Biol. Rep.* 27:388-389, Springer-Verlag, United States (2009).

Siripornadulsil, S., et al., "Microalgal Vaccine"in *Transgenic Microalgae as Green Cell Factories* 122-128, León, R. and Galvín, A., Eds., Landes Bioscience and Springer Science + Business Media, United States (2007).

Tanabayashi, K., et al., "Expression of Mumps Virus Glycoproteins in Mammalian Cells from Cloned cDNAs: Both F and HN Proteins Are Required for Cell Fusion," *Virology* 187(2):801-804, Academic Press, United States (1992).

International Search Report with Written Opinion for International Patent Application No. PCT/US10/62274, International Searching Authority, United States, mailed Mar. 16, 2011.

International Search Report for International Patent Application No. PCT/US2010/062209, International Searching Authority, United States, mailed Mar. 11, 2011.

Wang et al, Expression and characterization of soluble human parainfluenza virus type 1 hemagglutinin-neuraminidase glycoprotein, Journal of Virological Methods,98, 2001 53-61.

Paterson et al, Expression at the cell surface of biologically active fusion and hemagglutinin/neuraminidase proteins of the paramyxovirus simian virus 5 from cloned cDNA, Proc. Natl. Acad. Sci. USA, vol. 82, pp. 7520-7524, Nov. 1985.

\* cited by examiner

```
GGATCCATGGACCGTGTCGTCTCCCGCGTGGTCCTCGAGAACGAGGAGCGTGAGGCC
AAGAACACCTGGCGCCTTGTCTTTCGTGTCGCCGTCCTCTCCCTTATTGTCATGACCCT
CGCCATCTCCGTCGCCGCCCTCGTCTACAGCATGGAGGCTAGCACCCCCAACGATCTC
GCCGGAATCTCGACTGTTATCTCCCGCGCCGAGGACCGCGTCACCTCCCTCCTCAACT
CCAACCAGGATGTCGTTGATCGCGTCTACAAGCAGGTCGCCCTCGAGTCCCTCTCGC
CCTCCTTAACACCGAGAGCATCATTATGAACGCCATTACCTCCCTCAGCTACCAGATTA
ACGGCGCCGCCAACTCGTCCGGCTGCGGCGCCCCGTCCATGACCCTGATTACATCG
GCGGCGTCGGCAAGGAGCTCATCGTCGACGACACTAGCGATGCCACGTCCTTCTACC
CTAGCGCCTACCAGGAGCACCTCAACTTCATCCCTGCCCCCACTACCGGCTCCGGCTG
CACCCGCATTCCCAGCTTCGACATGTCCGCCACTCACTACTGCTACACCCATAACGTCA
TCCTTTCGGGTTGCCGCGACCACTCCCACAGCCACCAGTACCTCGCCCTCGGAGTTCT
TCGTACGTCCGCCACCGGCCGCGTCTTTTTTTCCACCCTCCGCAGCATCAACCTCGAC
GATACCCAGAACCGCAAGAGCTGCTCGGTCTCCGCCACCCCGCTCGGCTGCGACATG
CTCTGCTCCAAGGTCACCGAGACGGAGGAGGAGGATTACAAGTCCGTTACCCCCACTT
CGATGGTCCACGGCCGCCTTGGCTTCGACGGCCAGTACCACGAGAAGGACCTCGACG
TCACCGTTCTCTTTAAGGACTGGGTTGCCAACTACCCCGGCGTCGGCGGCGGCTCCCT
CATCGATGACCGCGTCTGGTTTCCTGTCTACGGTGGTCTCAAGCCTAACAGCCCCTCC
GATACCGCCCAGGAGGGTAAGTACGTGATCTACAAGCGCTACAACAACACCTGCCCTG
ACGAGCAGGATTACCAGGTCCGCATGGCCAAGTCCTCGTACAAGCCCGGTCGTTTCGG
CGGCAAGCGCGTCCAGCAGGCCATTCTCTCGATCAAGGTCTCGACCAGCCTCGGAGA
GGACCCCGTGCTCACCGTTCCCCCTAACACCGTCACCCTTATGGGCGCCGAGGGCCG
CATCCTCACCGTCGGTACCTCCCACTTCCTCTACCAGCGCGGCTCGAGCTACTTTTCCC
CTGCCCTTCTTTACCCCATGACTGTTCGCAACAAGACTGCTACCCTCCACAGCCCCTAC
ACCTTTAACGCCTTCACGCGCCCCGGAAGCGTCCCCTGCCAGGCGAGCGCCCGCTGC
CCTAACTCCTGCATTACCGGCGTCTACACCGACCCTTACCCTGTCGTCTTTCACCGCAA
CCATACCCTTCGCGGCGTCTTCGGTACTATGCTTGATAACGAGCAGGCCCGCCTCAAC
CCCGTCTCCGCCATTTTCGACTACACTTCCCGCTCCCGTATCACCCGCGTCTCCTCCAC
CTCCACCAAGGCCGCCTACACCACCTCCACCTGCTTTAAGGTTGTCAAGACTAACAAG
GTCTACTGCCTCTCCATCGCCGAGATTAGCAACACCCTCTTCGGAGAGTTCCGCATTGT
CCCCCTGCTCGTCGAGATCCTCAAGGACGATCGCGTTTAACATATG
```

(SEQ ID NO:1)

FIG. 1

| AA* | Codon | Fraction | AA* | Codon | Fraction | AA* | Codon | Fraction | AA* | Codon | Fraction |
|---|---|---|---|---|---|---|---|---|---|---|---|
| Ala | GCC | 0.64 | End | TAA | 0.34 | Leu | CTT | 0.16 | Ser | TCG | 0.33 |
| Ala | GCA | 0.03 | End | TGA | 0.33 | Leu | TTG | 0.02 | Ser | TCC | 0.31 |
| Ala | GCT | 0.18 | End | TAG | 0.33 | Leu | CTG | 0.12 | Ser | AGT | 0.03 |
| Ala | GCG | 0.16 | Gln | CAA | 0.08 | Leu | CTC | 0.69 | Ser | TCA | 0 |
| Arg | CGG | 0.01 | Gln | CAG | 0.92 | Leu | TTA | 0 | Ser | TCT | 0.09 |
| Arg | AGA | 0 | Glu | GAA | 0.09 | Leu | CTA | 0 | Thr | ACG | 0.3 |
| Arg | CGC | 0.8 | Glu | GAG | 0.91 | Lys | AAA | 0.04 | Thr | ACC | 0.54 |
| Arg | CGA | 0.01 | Gly | GGA | 0.1 | Lys | AAG | 0.96 | Thr | ACA | 0.02 |
| Arg | AGG | 0 | Gly | GGT | 0.2 | Met | ATG | 1 | Thr | ACT | 0.14 |
| Arg | CGT | 0.17 | Gly | GGG | 0 | Phe | TTT | 0.45 | Trp | TGG | 1 |
| Asn | AAC | 0.94 | Gly | GGC | 0.7 | Phe | TTC | 0.55 | Tyr | TAC | 0.94 |
| Asn | AAT | 0.06 | His | CAC | 0.83 | Pro | CCT | 0.21 | Tyr | TAT | 0.06 |
| Asp | GAT | 0.24 | His | CAT | 0.17 | Pro | CCG | 0.34 | Val | GTC | 0.62 |
| Asp | GAC | 0.76 | Ile | ATC | 0.7 | Pro | CCC | 0.43 | Val | GTA | 0 |
| Cys | TGC | 0.95 | Ile | ATA | 0 | Pro | CCA | 0.02 | Val | GTT | 0.14 |
| Cys | TGT | 0.05 | Ile | ATT | 0.3 | Ser | AGC | 0.24 | Val | GTG | 0.24 |

* AA=Amino Acid

Species: Newcastle disease virus
Name: Hemagglutinin-neuraminidase
Identified by 32 peptides covering 68% of the protein sequence 1 mdrvvsrvvl eneereaknt wrlvfrvavl slivmtlais vaalvysmea stpndlagis 61 tvisraedrv tsllnsnqdv vdrvykqval esplallnte siimnaitsl syqingaans 121 sgcgapvhdp dyiggvgkel ivddtsdats fypsayqehl nfipapttgs gctripsfdm 181 sathycythn vilsgcrdhs hshqylalgv lrtsatgrvf fstlrsinld dtqnrkscsv 241 satplgcdml cskvteteee dyksvtptsm vhgrlgfdgq yhekdldvtv lfkdwvanyp 301 gvgggslidd rvwfpvyggl kpnspsdtaq egkyviykry nntcpdeqdy qvrmakssyk 361 pgrfggkrvq qailsikvst slgedpvltv ppntvtlmga egriltvgts hflyqrgssy 421 fspallypmt vrnktatlhs pytfnaftrp gsvpcqasar cpnscitgvy tdpypvvfhr 481 nhtlrgvfgt mldneqarln pvsaifdyts rsritrvsst stkaayttst cfkvvktnkv 541 yclsiaeisn tlfgefrivp llveilkddr v (SEQ ID NO: 2)

FIG. 5

| Proposed Structure | Mass [M+Na] | Charge State [z] | 23 |
|---|---|---|---|
| $Hex_5HexNAc_2$ | 1579<br>802 | 1<br>2 | √ |
| $Hex_6HexNAc_2$ | 1783<br>903 | 1<br>2 | √ |
| $Hex_7HexNAc_2$ | 1987<br>1005 | 1<br>2 | √ |
| $Hex_8HexNAc_2$ | 1108 | 2 | √ |
| $Hex_9HexNAc_2$ | 1210 | 2 | √ |
| $Hex_{10}HexNAc_2$ | 1312 | 2 | √ |

FIG. 8

*Schizochytrium* Predicted Signal Anchor Sequences alpha-1,3 mannosyl-beta-1,2-GlcNac-transferase-I-like protein #1

MRGPGMVGLSRVDREHLRRRQQQAASEWRRWGFFVATAVVLLVFLTVYPNV (SEQ ID NO: 3)

ATGCGCGGCCCGGGCATGGTCGGCCTCAGCCGCGTGGACCGCGAGCACCTGCGGCGGCG
GCAGCAGCAGGCGGCGAGCGAATGGCGGCGCTGGGGGTTCTTCGTCGCGACGGCCGTCG
TCCTGCTCGTCTTTCTCACCGTATACCCGAACGTA (SEQ ID NO: 4)

beta-1,2-xylosyltransferase-like protein #1

MRTRGAAYVRPGQHEAKALSSRSSDEGYTTVNVVRTKRKRTTVAALVAAALLVTGFIVVVV
FVVVV (SEQ ID NO: 5)

ATGCGCACGCGGGGCGCGGCGTACGTGCGGCCGGGACAGCACGAGGCGAAGGCGCTCTC
GTCAAGGAGCAGCGACGAGGGATATACGACGGTCAACGTTGTCAGGACCAAGCGAAAG
AGGACCACTGTAGCCGCGCTTGTAGCCGCGGCGCTGCTGGTGACGGGCTTTATCGTCGTC
GTCGTCTTCGTCGTCGTTGTT (SEQ ID NO: 6)

beta-1,4-xylosidase-like protein

MEALREPLAAPPTSARSSVPAPLAKEEGEEEDGEKGTFGAGVLGVVAVLVIVVFAIVAGGGG
DI (SEQ ID NO: 7)

ATGGAGGCCCTGCGCGAGCCCTTGGCTGCGCCGCCAACGTCGGCGCGATCGTCGGTGCC
AGCGCCGCTCGCGAAGGAGGAGGGgAGGAGGAGGACGGGGAAAAaGGGACGTTTGGG
GCGGGGGTCCTCGGTGTCGTGGCGGTGCTCGTCATCGTGGTGTTTGCGATCGTGGCGGGA
GGCGGAGGCGATATT (SEQ ID NO: 8)

Galactosyltransferase-like protein #5

MLSVAQVAGSAHSRPRRGGERMQDVLALEESSRDRKRATARPGLYRALAILGLPLIVFIVWQ
MTSSLTTAPSA (SEQ ID NO: 9)

ATGTTGAGCGTaGCACAAGTCGCGGGGTCGGCCCACTCGCGGCCGAGACGAGGTGGTGA
GCGGATGCAAGACGTGCTGGCCCTGGAGGAAAGCAGCAGAGATCGAAAACGAGCAACA
GCAAGGCCCGGGCTATATCGCGCACTTGCGATTCTGGGGCTGCCGCTCATCGTATTCATC
GTATGGCAAATGACTAgCTCCCTCACGACTGCCCCGAGCGCC (SEQ ID NO: 10)

FIG. 10

PRODUCTION OF HEMAGGLUTININ-NEURAMINIDASE PROTEIN IN MICROALGAE

CROSS-REFERENCE TO RELATED APPLICATION

This application claims the benefit of the filing date of U.S. Appl. No. 61/290,469, filed Dec. 28, 2009. This application also claims the benefit of the U.S. provisional application filed Dec. 28, 2009, titled "Recombinant NDV Antigen and Uses Thereof," attorney reference number MER 09-139P, which is incorporated by reference herein in its entirety.

REFERENCE TO A SEQUENCE LISTING SUBMITTED ELECTRONICALLY

The content of the electronically submitted sequence listing ("Sequence Listing ascii.txt", 16,932 bytes, created on Dec. 28, 2010) filed with the application is incorporated herein by reference in its entirety.

BACKGROUND OF THE INVENTION

1. Field of the Invention

The present invention is directed to recombinant microalgal cells and their use in production of hemagglutinin-neuraminidase (HN) polypeptides, as well as compositions and uses thereof.

2. Background

Production of proteins via the fermentation of microorganisms presents several advantages over existing systems such as plant and animal cell culture. For example, microbial fermentation-based processes can offer (i) rapid production of high concentration of protein; (ii) the ability to use sterile, well-controlled production conditions (such as Good Manufacturing Practice (GMP) conditions); (iii) the ability to use simple, chemically defined growth media allowing for simpler fermentations and fewer impurities; (iv) the absence of contaminating human or animal pathogens; and (v) the ease of recovering the protein (e.g., via isolation from the fermentation media). In addition, fermentation facilities are typically less costly to construct than cell culture facilities.

Microalgae, such as thraustochytrids, can be grown with standard fermentation equipment, with very short culture cycles (e.g., 1-5 days), inexpensive defined media and minimal purification, if any. Furthermore, certain microalgae, e.g., *Schizochytrium*, have a demonstrated history of safety for food applications of both the biomass and lipids derived therefrom. For example, DHA-enriched triglyceride oil from this microorganism has received GRAS (Generally Recognized as Safe) status from the U.S. Food and Drug Administration.

Microalgae have been shown to be capable of expressing recombinant proteins. For example, U.S. Pat. No. 7,001,772 discloses the first recombinant constructs suitable for transforming thraustochytrids, including members of the genus *Schizochytrium*. This publication discloses, among other things, *Schizochytrium* nucleic acid and amino acid sequences for an acetolactate synthase, an acetolactate synthase promoter and terminator region, an α-tubulin promoter, a promoter from a polyketide synthase (PKS) system, and a fatty acid desaturase promoter. U.S. Publ. Nos. 2006/0275904 and 2006/0286650, subsequently discloses *Schizochytrium* sequences for actin, elongation factor 1 alpha (ef1α), and glyceraldehyde 3-phosphate dehydrogenase (gapdh) promoters and terminators.

Viral vaccines are often made from inactivated or attenuated preparations of viral cultures corresponding to the disease they are intended to prevent. Generally, a virus is cultured from the same or similar cell type as the virus might infect in the wild. Such cell culture is expensive and often difficult to scale. To address this problem, attempts have been made to express viral protein antigens in transgenic hosts, which can be less costly to culture and more amenable to scale. However, viral membrane proteins such as hemagglutinin-neuraminidase (HN) protein can be very difficult to produce in large amounts, and attempts to express viral envelope proteins in whole or in part in heterologous systems have often been met with limited success. Thus, there is a need for new heterologous expression systems, such as those of the present invention, that are scaleable and able to produce viral HN antigens.

BRIEF SUMMARY OF THE INVENTION

The present invention is directed to a method for production of a hemagglutinin-neuraminidase (HN) polypeptide, comprising culturing a recombinant microalgal host cell in a medium, wherein the recombinant microalgal host cell comprises a nucleic acid molecule comprising a polynucleotide sequence that encodes a heterologous HN polypeptide, to produce the heterologous FIN polypeptide. In some embodiments, the HN polypeptide is secreted. In some embodiments, the method further comprises recovering the HN polypeptide from the medium. In some embodiments, the FIN polypeptide is at least 90% identical to SEQ ID NO: 2 or SEQ ID NO: 11. In some embodiments, the polynucleotide sequence encoding the HN polypeptide further comprises a membrane domain.

The present invention is directed to a method of producing a composition comprising a heterologous HN polypeptide, the method comprising: (a) expressing a heterologous HN polypeptide in a microalgal host cell, and (b) culturing the microalgal host cell under conditions sufficient to produce the heterologous HN polypeptide, wherein the composition is produced as the culture supernatant comprising the heterologous HN polypeptide. In some embodiments, the method further comprises removing the culture supernatant from the composition and resuspending the heterologous HN polypeptide in an aqueous liquid carrier.

In some embodiments, the host cell of any of the above-described methods is a Labyrinthulomycota host cell. In some embodiments, the host cell of any of the above-described methods is a *Schizochytrium* or a *Thraustochytrium* host cell.

The present invention is directed to a recombinant microalgal cell, comprising a nucleic acid molecule comprising a polynucleotide sequence that encodes a heterologous HN protein. In some embodiments, the HN protein is at least 90% identical to SEQ ID NO: 2 or SEQ ID NO: 11. In some embodiments, the polynucleotide sequence that encodes the HN protein further comprises a membrane domain. In some embodiments, the microalgal cell is a Labyrinthulomycota cell. In some embodiments, the microalgal cell is a *Schizochytrium* or a *Thraustochytrium* cell.

BRIEF DESCRIPTION OF THE DRAWINGS

FIG. 1 shows the polynucleotide sequence (SEQ ID NO: 1) that encodes hemagglutinin-neuraminidase (HN) protein of Newcastle disease virus, optimized for expression in *Schizochytrium* sp. ATCC 20888.

FIG. 2 shows a codon usage table for *Schizochytrium*.

FIG. 3 shows a plasmid map of pCL0081 [pEPCT(+)-caliNDV_HN], also termed pCL0081.

FIG. 4 shows secretion of HN protein by transgenic *Schizochytrium* CL0081-23 ("23"). The centrifugation procedure for isolating the low-speed supernatant and the insoluble fraction is shown in FIG. 4A. The recovered recombinant HN protein (as indicated by an arrow) is shown in Coomassie stained gels ("Coomassie") and anti-NDV immunoblots ("IB: anti-NDV") from the low-speed supernatant in FIG. 4B and the insoluble fraction in FIG. 4C. A co-purifying actin band is indicated by an asterisk.

FIG. 5 shows peptide sequence analysis for the recovered recombinant HN protein, which was identified by a total of 32 peptides covering 68% of the protein sequence (SEQ ID NO: 2). The tryptic sites are underlined.

Figure 6:
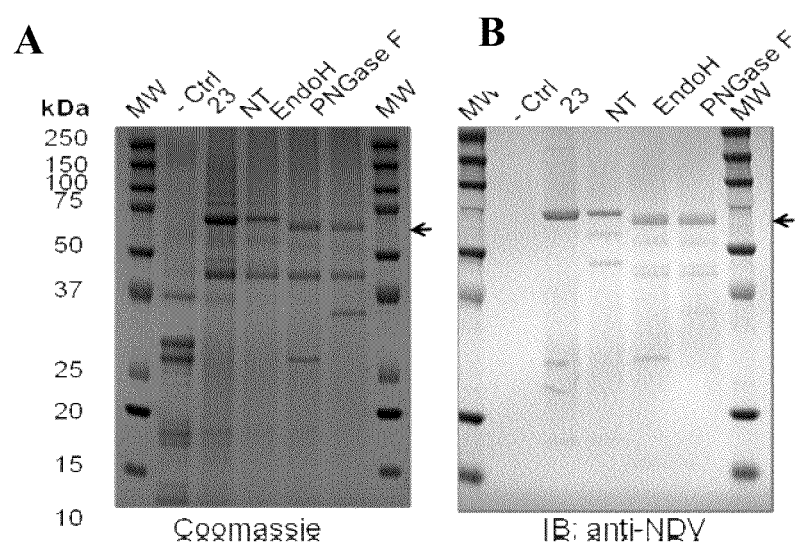
FIG. 6A and FIG. 6B show a Coomassie stained gel ("Coomassie") and anti-NDV immunoblots ("IB: anti-NDV") illustrating HN protein glycosylation in *Schizochytrium*. "-Ctrl" refers to the negative control for immunoblotting, which was the transgenic *Schizochytrium* AB0018. "23" refers to transgenic *Schizochytrium* cl0081-23. "EndoH" and "PNGase F" refer to enzymatic treatments of the insoluble fraction of transgenic *Schizochytrium* CL0081-23 with the respective enzymes. "NT" refers to transgenic *Schizochytrium* CL0081-23 incubated without enzymes but under the same conditions as the EndoH and PGNase F treatments.

FIG. 7 shows N-glycan structures detected on native *Schizochytrium* secreted proteins as determined by total ion mapping.

FIG. 8 shows glycan species obtained by NSI-total ion mapping.

FIG. 9 shows hemagglutination activity of HN from transgenic *Schizochytrium* CL0081-23 ("23") supernatant. "[protein]" refers to the concentration of protein, decreasing from left to right with increasing dilutions of the samples. "-" refers to negative control lacking HN. "+" refers to Influenza hemagglutinin positive control. "HAU" refers to Hemagglutinin Activity Unit based on the fold dilution of samples from left to right. "2" refers to a two-fold dilution of the sample in the first well; subsequent wells from left to right represent doubling dilutions over the previous well, such that the fold dilutions from the first to last wells from left to right were 2, 4, 8, 16, 32, 64, 128, 256, 512, 1024, 2048, and 4096.

FIG. 10 shows predicted signal anchor sequences native to *Schizochytrium* based on use of the SignalP algorithm. See, e.g., Bendsten et al., *J, Mol. Biol.* 340: 783-795 (2004); Nielsen, H. and Krogh, A. *Proc. Int. Conf. Intell. Syst. Mol. Biol.* 6: 122-130 (1998); Nielsen, H., et al., *Protein Engineering* 12: 3-9 (1999); Emanuelsson, O. et al., *Nature Protocols* 2: 953-971 (2007).

DETAILED DESCRIPTION OF THE INVENTION

The present invention is directed to the production of heterologous hemagglutinin-neuraminidase (HN) polypeptides in microalgal host cells. The present invention is also directed to microalgal host cells comprising the heterologous HN polypeptides, HN polypeptides produced from the microalgal host cells, as well as compositions and uses thereof.

Microalgal Host Cells

Microalgae, also known as microscopic algae, are often found in freshwater and marine systems. Microalgae are unicellular but can also grow in chains and groups. Individual cells range in size from a few micrometers to a few hundred micrometers. Because the cells are capable of growing in aqueous suspensions, they have efficient access to nutrients and the aqueous environment.

In some embodiments, the microalgal host cell is a heterokont or stramenopile.

In some embodiments, the microalgal host cell is a member of the phylum Labyrinthulomycota. In some embodiments, the Labyrinthulomycota host cell is a member of the order Thraustochytriales or the order Labyrinthulales. According to the present invention, the term "thraustochytrid" refers to any member of the order Thraustochytriales, which includes the family Thraustochytriaceae, and the term "labyrinthulid" refers to any member of the order Labyrinthulales, which includes the family Labyrinthulaceae. Members of the family Labyrinthulaceae were previously considered to be members of the order Thraustochytriales, but in more recent revisions of the taxonomic classification of such organisms, the family Labyrinthulaceae is now considered to be a member of the order Labyrinthulales. Both Labyrinthulales and Thraustochytriales are considered to be members of the phylum Labyrinthulomycota. Taxonomic theorists now generally place both of these groups of microorganisms with the algae or algae-like protists of the Stramenopile lineage. The current taxonomic placement of the thraustochytrids and labyrinthulids can be summarized as follows:

Realm: Stramenopila (Chromista)
  Phylum: Labyrinthulomycota (Heterokonta)
    Class: Labyrinthulomycetes (Labyrinthulae)
      Order: Labyrinthulales
        Family: Labyrinthulaceae
      Order: Thraustochytriales
        Family: Thraustochytriaceae For purposes of the present invention, strains described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporum*), *Japonochytrium* (Species: sp., *marinum*), *Aplanochytrium* (Species: sp., *haliotidis, kerguelensis, profunda, stocchinoi*), *Althornia* (Species: sp., *crouchii*), or *Elina* (Species: sp., *marisalba, sinorifica*). For the purposes of this invention, species described within *Ulkenia* will be considered to be members of the genus *Thraustochytrium*. *Aurantiochytrium, Oblongichytrium, Botryochytrium, Parietichytrium*, and *Sicyoidochytrium* are additional genuses encompassed by the phylum Labyrinthulomycota in the present invention.

Strains described in the present invention as Labyrinthulids include the following organisms: Order: Labyrinthulales, Family: Labyrinthulaceae, Genera: *Labyrinthula* (Species: sp., *algeriensis, coenocystis, chattonii, macrocystis, macrocystis atlantica, macrocystis macrocystis, marina, minuta, roscoffensis, valkanovii, vitellina, vitellina pacifica, vitellina vitellina, zopfii*), *Labyrinthuloides* (Species: sp., *haliotidis, yorkensis*), *Labyrinthomyxa* (Species: sp., *marina*), *Diplophrys* (Species: sp., *archeri*), *Pyrrhosorus* (Species: sp., *marinus*), *Sorodiplophrys* (Species: sp., *stercorea*) or *Chlamydomyxa* (Species: sp., *labyrinthuloides, montana*) (although there is currently not a consensus on the exact taxonomic placement of *Pyrrhosorus, Sorodiplophrys* or *Chlamydomyxa*).

Microalgal cells of the phylum Labyrinthulomycota include, but are not limited to, deposited strains PTA-10212, PTA-10213, PTA-10214, PTA-10215, PTA-9695, PTA-9696, PTA-9697, PTA-9698, PTA-10208, PTA-10209, PTA-10210, PTA-10211, the microorganism deposited as SAM2179 (named "*Ulkenia* SAM2179" by the depositor), any *Thraustochytrium* species (including former *Ulkenia* species such as *U. visurgensis, U. amoeboida, U. sarkariana, U. profunda, U radiata, U. minuta* and *Ulkenia* sp. BP-5601), and including *Thraustochytrium striatum, Thraustochytrium aureum, Thraustochytrium roseum*; and any *Japonochytrium* species. Strains of Thraustochytriales include, but are not limited to *Thraustochytrium* sp. (23B) (ATCC 20891); *Thraustochytrium striatum* (Schneider) (ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207). *Schizochytrium* include, but are not limited to *Schizochytrium aggregatum, Schizochytrium limacinum, Schizochytrium* sp. (S31) (ATCC 20888), *Schizochytrium* sp. (S8) (ATCC 20889), *Schizochytrium* sp. (LC-RM) (ATCC 18915), *Schizochytrium* sp. (SR 21), deposited strain ATCC 28209, and deposited *Schizochytrium limacinum* strain IFO 32693. In some embodiments, the cell is a *Schizochytrium* or a *Thraustochytrium*. *Schizochytrium* can replicate both by successive bipartition and by forming sporangia, which ultimately release zoospores. *Thraustochytrium*, however, replicate only by forming sporangia, which then release zoospores.

In some embodiments, the microalgal host cell is a thraustochytrid. In some embodiments, the microalgal host cell is a *Schizochytrium* or *Thraustochytrium* cell.

In some embodiments, the microalgal host cell is a labyrinthulid.

In some embodiments, the microalgal host cell contains a recombinant vector comprising a nucleic acid sequence encoding a selection marker. In some embodiments, the selection marker allows for the selection of transformed microorganisms. In some embodiments, the selection marker is an auxotrophic marker, a dominant selection marker (such as, for example, an enzyme that degrades antibiotic activity), or another protein involved in transformation selection.

According to the present invention, the term "transformation" is used to refer to any method by which an exogenous nucleic acid molecule (i.e., a recombinant nucleic acid molecule) can be inserted into microbial cells. In microbial systems, the term "transformation" is used to describe an inherited change due to the acquisition of exogenous nucleic acids by the microorganism and is essentially synonymous with the term "transfection." Suitable transformation techniques for introducing exogenous nucleic acid molecules into the Labyrinthulomycota host cells include, but are not limited to, particle bombardment, electroporation, microinjection, lipofection, adsorption, infection, and protoplast fusion. In some embodiments, exogenous nucleic acid molecules, including recombinant vectors, are introduced into a microbial cell that is in a stationary phase.

In some embodiments of the invention, the microalgal host cell is genetically modified to introduce or delete genes involved in biosynthetic pathways associated with the transport and/or synthesis of carbohydrates, including those involved in glycosylation. For example, the host cell can be modified by deleting endogenous glycosylation genes and/or inserting human or animal glycosylation genes to allow for glycosylation patterns that more closely resemble those of humans. Modification of glycosylation in yeast is shown, for example, in U.S. Pat. No. 7,029,872 and U.S. Publ. Nos. 2004/0171826, 2004/0230042, 2006/0257399, 2006/0029604, and 2006/0040353. In some embodiments, the microalgal host cell includes a cell in which RNA viral elements are employed to increase or regulate gene expression.

Effective culture conditions for the microalgal host cells include, but are not limited to, effective media, bioreactor, temperature, pH, and oxygen conditions that permit protein production and/or recombination. An effective medium refers to any medium in which a microalgal cell is typically cultured. Such medium typically comprises an aqueous medium having assimilable carbon, nitrogen, and phosphate sources, as well as appropriate salts, minerals, metals, and other nutrients, such as vitamins. Non-limiting culture conditions suitable for Thraustochytriales microorganisms are described, for example, in U.S. Pat. No. 5,340,742. Cells of the present invention can be cultured in conventional fermentation bioreactors, shake flasks, test tubes, microtiter dishes, and petri plates. Culturing can be carried out at a temperature, pH, and oxygen content appropriate for a recombinant cell.

Non-limiting fermentation conditions for thraustochytrid host cells are shown below in Table 1:

TABLE 1

| Vessel Media | | | |
|---|---|---|---|
| Ingredient | Concentration | | Ranges |
| Na$_2$SO$_4$ | g/L | 13.62 | 0-50, 15-45, or 25-35 |
| K2SO4 | g/L | 0.72 | 0-25, 0.1-10, or 0.5-5 |
| KCl | g/L | 0.56 | 0-5, 0.25-3, or 0.5-2 |
| MgSO$_4$•7H$_2$O | g/L | 2.27 | 0-10, 1-8, or 2-6 |
| (NH$_4$)$_2$SO$_4$ | g/L | 17.5 | 0-50, 0.25-30, or 5-20 |
| CaCl$_2$*2H$_2$O | g/L | 0.19 | 0.1-5, 0.1-3, or 0.15-1 |
| KH$_2$PO$_4$ | g/L | 6.0 | 0-20, 0.1-10, or 1-7 |
| Post autoclave (Metals) | | | |
| Citric acid | mg/L | 3.50 | 0.1-5000, 1-3000, or 3-2500 |
| FeSO$_4$•7H$_2$O | mg/L | 51.5 | 0.1-1000, 1-500, or 5-100 |
| MnCl$_2$•4H$_2$O | mg/L | 3.10 | 0.1-100, 1-50, or 2-25 |
| ZnSO$_4$•7H$_2$O | mg/L | 6.20 | 0.1-100, 1-50, or 2-25 |
| CoCl$_2$•6H$_2$O | mg/L | 0.04 | 0-1, 0.001-0.1, or 0.01-0.1 |
| Na$_2$MoO$_4$•2H$_2$O | mg/L | 0.04 | 0.001-1, 0.005-0.5, or 0.01-0.1 |
| CuSO$_4$•5H$_2$O | mg/L | 2.07 | 0.1-100, 0.5-50, or 1-25 |
| NiSO$_4$•6H$_2$O | mg/L | 2.07 | 0.1-100, 0.5-50, or 1-25 |
| Post autoclave (Vitamins) | | | |
| Thiamine** | mg/L | 9.75 | 0.1-100, 1-50, or 5-25 |
| Vitamin B12** | mg/L | 0.16 | 0.01-100, 0.05-5, or 0.1-1.0 |
| Ca½-pantothenate** | mg/L | 3.33 | 0.1-100, 0.1-50, or 1-10 |
| Post autoclave (Carbon) | | | |
| Glucose | g/L | 20.0 | 5-150, 10-100, or 20-50 |
| Nitrogen Feed: | | | |
| NH$_4$OH | mL/L | 23.6 | 5-150, 10-100, 15-50 |

**filter sterilized and added post-autoclave

General cultivation conditions include the following:

| | |
|---|---|
| pH: | 5.5-9.5, 6.5-8.0, or 6.3-7.3 |
| temperature: | 15° C.-45° C., 18° C.-35° C., or 20° C.-30° C. |
| dissolved oxygen: | 0.1%-100% saturation, 5%-50% saturation, or 10%-30% saturation |
| glucose controlled: | 5 g/L-100 g/L, 10 g/L-40 g/L, or 15 g/L-35 g/L. |

Polypeptides

The present invention is also directed to a microalgal host cell comprising a heterologous HN polypeptide, as well as a HN polypeptide produced therefrom. The term "heterologous" as used herein refers to a sequence or polypeptide, for example, that is not naturally found in the microalgal host cell.

The term "polypeptide" includes single-chain polypeptide molecules as well as multiple-polypeptide complexes where individual constituent polypeptides are linked by covalent or non-covalent means. According to the present invention, an isolated polypeptide is a polypeptide that has been removed from its natural milieu (i.e., that has been subject to human manipulation) and can include purified proteins, purified peptides, partially purified proteins, partially purified peptides, recombinantly produced proteins or peptides, and synthetically produced proteins or peptides, for example.

In some embodiments the heterologous HN polypeptide comprises a membrane domain. The term "membrane domain" as used herein refers to any domain within a polypeptide that targets the polypeptide to a membrane and/or allows the polypeptide to maintain association with a membrane and includes, but is not limited to, a transmembrane domain (e.g., a single or multiple membrane spanning region), an integral monotopic domain, a signal anchor sequence, an ER signal sequence, an N-terminal or internal or C-terminal stop transfer signal, a glycosylphosophatidylinositol anchor, and combinations thereof. A membrane domain can be located at any position in the polypeptide, including the N-terminal, C-terminal, or middle of the polypeptide. A membrane domain can be associated with permanent or temporary attachment of a polypeptide to a membrane. In some embodiments, a membrane domain can be cleaved from a membrane protein. In some embodiments, the membrane domain is a signal anchor sequence. In some embodiments, the membrane domain is any of the signal anchor sequences shown in FIG. 10, or an anchor sequence derived therefrom. In some embodiments, the membrane domain is a viral signal anchor sequence.

In some embodiments, the heterologous HN polypeptide comprises a membrane domain that is a native HN protein membrane domain. HN is a Type II membrane protein containing a single membrane domain, in which the C-terminus is extracellular and the N-terminus is cytoplasmic. The N-terminus further comprises a signal anchor sequence.

In some embodiments, the heterologous HN polypeptide does not comprise a native membrane domain but has been recombinantly fused to a heterologous membrane domain. In some embodiments, the membrane domain is a microalgal membrane domain. In some embodiments, the membrane domain is a Labyrinthulomycota membrane domain. In some embodiments, the membrane domain is a thraustochytrid membrane domain. In some embodiments, the membrane domain is a *Schizochytrium* or *Thraustochytrium* membrane domain. In some embodiments, the membrane domain comprises a signal anchor sequence from *Schizochytrium* alpha-1,3-mannosyl-beta-1,2-GlcNac-transferase-I-like protein #1 (SEQ ID NO:3), *Schizochytrium* beta-1,2-xylosyltransferase-like protein #1 (SEQ ID NO:5), *Schizochytrium* beta-1,4-xylosidase-like protein (SEQ ID NO:7), or *Schizochytrium* galactosyltransferase-like protein #5 (SEQ ID NO:9).

In some embodiments, the heterologous membrane domain is from a different type of membrane protein than the HN protein. As described by Chou and Elrod, *Proteins: Structure, Function and Genetics* 34:137-153 (1999), for example, other types of membrane proteins include:

1) Type 1 membrane proteins: These proteins have a single transmembrane domain in the mature protein. The N-terminus is extracellular, and the C-terminus is cytoplasmic. The proteins are subdivided into Type Ia (containing a cleavable signal sequence) and Type Ib (without a cleavable signal sequence).
2) Multipass transmembrane proteins: In Type I and II membrane proteins the polypeptide crosses the lipid bilayer once, whereas in multipass membrane proteins the polypeptide crosses the membrane multiple times. Multipass transmembrane proteins are also subdivided into Types Ma and Mb. Type IIIa proteins have cleavable signal sequences. Type IIIb proteins have their amino termini exposed on the exterior surface of the membrane, but do not have a cleavable signal sequence.
3) Lipid chain anchored membrane proteins: These proteins are associated with the membrane bilayer by means of one or more covalently attached fatty acid chains or other types of lipid chains called prenyl groups.
4) GPI-anchored membrane proteins: These proteins are bound to the membrane by a glycosylphosphatidylinositol (GPI) anchor.
5) Peripheral membrane proteins: These proteins are bound to the membrane indirectly by noncovalent interactions with other membrane proteins.

In some embodiments, the heterologous membrane domain is from a different Type II membrane protein than the HN protein. In some embodiments, the N-terminus of the heterologous Type II membrane domain comprises a signal anchor sequence.

In some embodiments, the heterologous HN polypeptide is a glycoprotein. In some embodiments, the heterologous HN polypeptide has a glycosylation pattern characteristic of expression in a Labyrinthulomycota cell. In some embodiments, the heterologous HN polypeptide has a glycosylation pattern characteristic of expression in a thraustochytrid cell. In some embodiments, a heterologous HN polypeptide expressed in the microalgal host cell is a glycoprotein having a glycosylation pattern that more closely resembles mammalian glycosylation patterns than proteins produced in yeast or *E. coli*. In some embodiments, the glycosylation pattern comprises a N-linked glycosylation pattern. In some embodiments, the glycoprotein comprises high-mannose oligosaccharides. In some embodiments, the glycoprotein is substantially free of sialic acid. The term "substantially free of sialic acid" as used herein means less than 10%, less than 9%, less than 8%, less than 7%, less than 6%, less than 5%, less than 4%, less than 3%, less than 2%, or less than 1% of sialic acid. In some embodiments, sialic acid is absent from the glycoprotein.

In some embodiments, the expression system used for expression of a heterologous HN polypeptide in the microalgal host cell comprises regulatory control elements that are active in microalgal host cells. In some embodiments, the expression system comprises regulatory control elements that are active in Labyrinthulomycota cells. In some embodiments, the expression system comprises regulatory control elements that are active in Labyrinthulae. In some embodiments, the expression system comprises regulatory control elements that are active in thraustochytrids. In some embodiments, the expression system comprises regulatory control elements that are active in *Schizochytrium* or *Thraustochytrium*. Many microalgal regulatory control elements, including various promoters, are active in a number of diverse species.

In some embodiments, the expression system used for expression of a heterologous HN polypeptide in the microalgal host cell comprises regulatory elements that are derived from microalgal sequences. In some embodiments, the expression system for expression of heterologous HN polypeptides in the microalgal host cell comprises regulatory elements that are derived from non-microalgal sequences. In some embodiments, the expression system comprises a polynucleotide sequence encoding a heterologous HN polypeptide, wherein the polynucleotide sequence is associated with any promoter sequence, any terminator sequence, and/or any other regulatory sequence that is functional in the microalgal host cell. Inducible or constitutively active sequences can be used.

The present invention also includes use of an expression cassette for expression of a heterologous HN polypeptide in the microalgal host cell. The design and construction of expression cassettes use standard molecular biology techniques known to persons skilled in the art. See, for example, Sambrook et al., 2001, Molecular Cloning: A Laboratory Manual, 3$^{rd}$ edition. In some embodiments, the microalgal host cell comprises an expression cassette containing genetic elements, such as at least a promoter, a coding sequence, and a terminator region operably linked in such a way that they are functional in the microalgal host cell. In some embodiments, the expression cassette comprises a polynucleotide sequence encoding a membrane domain. In some embodiments, the expression cassette comprises a polynucleotide sequence encoding a signal anchor sequence. In some embodiments, the polynucleotide sequence encoding a signal anchor sequence comprises SEQ ID NO:4, SEQ ID NO:6, SEQ ID NO:8, or SEQ ID NO:10.

In some embodiments, an isolated nucleic acid sequence encoding the heterologous HN polypeptide is operably linked to a promoter sequence and/or a terminator sequence, both of which are functional in the host cell. The promoter and/or terminator sequence to which the isolated nucleic acid sequence encoding the heterologous HN polypeptide to be expressed is operably linked to and can include any promoter and/or terminator sequence. Inducible or constitutively active regulatory sequences can be used. Regulatory sequences include but are not limited to the *Schizochytrium* regulatory sequences described in U.S. Publ. No. 2010/0233760, U.S. Pat. No. 7,001,772, and U.S. Publ. Nos. 2006/0275904 and 2006/0286650, such as: an OrfC promoter, an OrfC terminator, an EF1 short promoter, EF1 long promoter, a Sec1 promoter, 60S short promoter, 60S long promoter, an acetolactate synthase promoter, an acetolactate synthase terminator, an α-tubulin promoter, a promoter from a polyketide synthase (PKS) system, a fatty acid desaturase promoter, an actin promoter, an actin terminator, an elongation factor 1 alpha (ef1α) promoter, an ef1α terminator, a glyceraldehyde 3-phosphate dehydrogenase (gapdh) promoter, a gapdh terminator, and combinations thereof, or other regulatory sequences functional in the microalgal cell in which they are transformed that are operably linked to the polynucleotide sequence encoding the heterologous HN polypeptide. In some embodiments, the polynucleotide sequence encoding the heterologous HN polypeptide is operably linked to a polynucleotide encoding a membrane domain. In some embodiments, the polynucleotide sequence encoding the heterologous HN polypeptide is codon-optimized for the specific microalgal host cell to optimize translation efficiency.

In some embodiments, the microalgal host cells comprise a recombinant vector containing an expression cassette as described above. Recombinant vectors include, but are not limited to, plasmids, phages, and viruses. In some embodiments, the recombinant vector is a linearized vector. In some embodiments, the recombinant vector is an expression vector. As used herein, the phrase "expression vector" refers to a vector that is suitable for production of a heterologous HN polypeptide. In some embodiments, a polynucleotide sequence encoding the heterologous HN polypeptide is inserted into the recombinant vector to produce a recombinant nucleic acid molecule. In some embodiments, the recombinant vector comprises a selectable marker for the selection of a recombinant microalgal host cell comprising the recombinant vector. In some embodiments, the recombinant vector comprises a membrane domain that is operably linked to a heterologous HN polypeptide.

In some embodiments, the heterologous FIN polypeptide is a polypeptide comprising an amino acid sequence at least 90%, at least 91%, at least 92%, at least 93%, at least 94%, at least 95%, at least 96%, at least 97%, at least 98%, at least 99%, or 100% identical to a known HN sequence, e.g SEQ ID 2 or SEQ ID NO: 11. or a polynucleotide encoding a heterologous FIN polypeptide comprising an amino acid sequence at least 90%, at least 91%, at least 92%, at least 93%, at least 94%, at least 95%, at least 96%, at least 97%, at least 98%, at least 99%, or 100% identical to a known HN sequence, e.g., SEQ ID NO: 2or SEQ ID NO: 11, wherein the polypeptide is recognizable by an antibody that specifically binds to the HN sequence.

The present invention is also directed to a method for production of a heterologous HN polypeptide, comprising culturing a recombinant microalgal host cell in a medium, wherein the recombinant microalgal host cell comprises a nucleic acid molecule comprising a polynucleotide sequence that encodes a heterologous HN polypeptide, to produce the heterologous HN polypeptide.

In some embodiments, a heterologous HN polypeptide produced from a microalgal host cell is produced at commercial scale.

The present invention is also directed to a composition comprising a heterologous HN polypeptide produced from a microalgal host cell and an aqueous liquid carrier.

In some embodiments, a heterologous HN polypeptide is recovered from the culture medium or fermentation medium in which the microalgal host cell is grown. In some embodiments, a heterologous HN polypeptide produced from a microalgal host cell can be isolated in "substantially pure" form. As used herein, "substantially pure" refers to a purity that allows for the effective use of the heterologous HN polypeptide produced from a microalgal host cell as a commercial product.

The present invention is also directed to a method of producing a composition comprising a heterologous HN polypeptide, the method comprising: (a) expressing a heterologous HN polypeptide in a microalgal host cell, and (b) culturing the microalgal host cell under culture conditions sufficient to produce a microalgal host cell comprising the heterologous HN polypeptide, wherein the composition is produced as the culture supernatant comprising the heterologous HN polypeptide. In some embodiments, the method further comprises removing the culture supernatant and resuspending the heterologous HN polypeptide in an aqueous liquid carrier. In some embodiments, the composition is used as a vaccine.

In some embodiments, the microalgal host cells described herein express heterologous HN polypeptide that is free or substantially free of associated viral material, such as viral genetic material, other than the desired viral HN antigen. The term "substantially free of associated viral material" as used herein means less than 10%, less than 9%, less than 8%, less than 7%, less than 5%, less than 4%, less than 3%, less than 2%, or less than 1% of associated viral material.

The present invention is also directed to an NDV vaccine or composition which comprises an effective amount of a recombinant NDV HN antigen and a pharmaceutically or veterinarily acceptable carrier, excipient, or vehicle, wherein the recombinant NDV HN antigen is expressed in a microalgal cell. In some embodiments, the microalgal cell is a *Schizochytrium*. In some embodiments, the NDV HN antigen is partially purified, or substantially purified. In some embodiments, the NDV antigen is present in microalgae harvested in whole. In some embodiments, the NDV antigen is in the form of a "biomass" which is a lysate of the harvested microalgae. In some embodiments, the recombinant NDV HN antigen is expressed in a transgenic microalgal cell.

The present invention is also directed to a substantially purified NDV HN antigen expressed in microalgae.

The present invention is also directed to a microalgal cell or culture stably transformed with a gene for expressing an NDV HN polypeptide or fragment or variant thereof.

The present invention is also directed to a method of producing a polypeptide, comprising: (a) culturing within a microalgal culture medium a microalgal cell culture, wherein the microalgal cell culture is stably transformed to express the polypeptide, and wherein the polypeptide is expressed from a nucleotide sequence comprising a coding sequence for the polypeptide and: an operably linked coding sequence for a signal peptide that directs secretion of the polypeptide into the culture medium or an operably linked sequence associated with a membrane domain; and (b) collecting the polypeptide from the culture medium. In some embodiments, the membrane domain is the NDV HN membrane domain. The term collecting includes but is not limited to harvesting from the culture medium or purifying. After production of the recombinant polypeptide in microalgae, any method available in the art may be used for protein purification. The various steps include freeing the protein from the nonprotein or microalgal material, followed by the purification of the protein of interest from other proteins. Initial steps in the purification process include centrifugation, filtration or a combination thereof. Proteins secreted within the extracellular space of tissues can be obtained using vacuum or centrifugal extraction. Minimal processing could also involve preparation of crude products. Other methods include maceration and extraction in order to permit the direct use of the extract. Such methods to purify the protein of interest can exploit differences in protein size, physio-chemical properties, and binding affinity. Such methods include chromatography, including procainamide affinity, size exclusion, high pressure liquid, reversed-phase, and anion-exchange chromatography, affinity tags, filtration, etc. In particular, immobilized Niion affinity chromatography can be used to purify the expressed protein. See, Favacho et al., *Protein Expression and Purification* 46:196-203 (2006). See also, Zhou et al., *Protein J* 26:29-37 (2007); Wang et al., *Vaccine* 15:2176-2185 (2006); and WO/2009/076778. Protectants may be used in the purification process such as osmotica, antioxidants, phenolic oxidation inhibitors, protease inhibitors, and the like.

Methods of Using the Microalgal Host Cells and Heterologous HN Polypeptides

The present invention also includes the use of a microalgal host cell comprising a heterologous HN polypeptide, use of a heterologous HN polypeptide produced from a microalgal host cell, and compositions thereof, for therapeutic applications in animals or humans ranging from preventive treatments to disease.

The terms "treat" and "treatment" refer to both therapeutic treatment and prophylactic or preventative measures, wherein the object is to prevent or slow down (lessen) an undesired physiological condition, disease, or disorder, or to obtain beneficial or desired clinical results. For purposes of this invention, beneficial or desired clinical results include, but are not limited to, alleviation or elimination of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a clinically significant response without excessive side effects. Treatment also includes prolonging survival as compared to expected survival if not receiving treatment.

In some embodiments, heterologous HN polypeptides produced from microalgal host cells are recovered from the culture supernatant for direct use as an animal or human vaccine.

In some embodiments, heterologous HN polypeptides produced from microalgal host cells are purified according to the requirements of the use of interest, e.g., administration as a vaccine. For a typical human vaccine application, the low speed supernatant would undergo an initial purification by concentration (e.g., tangential flow filtration followed by ultrafiltration), chromatographic separation (e.g., anion-exchange chromatography), size exclusion chromatography, and sterilization (e.g., 0.2 μm filtration). In some embodiments, a vaccine of the invention lacks potentially allergenic carry-over proteins such as, for example, egg protein. In some embodiments, a vaccine comprising heterologous HN polypeptides produced from microalgal host cells lacks any viral material other than a viral HN polypeptide.

According to the disclosed methods, administration can be, for example, by intramuscular (i.m.), intravenous (i.v.), subcutaneous (s.c.), or intrapulmonary routes. Other suitable routes of administration include, but are not limited to intratracheal, transdermal, intraocular, intranasal, inhalation, intracavity, intraductal (e.g., into the pancreas), and intraparenchymal (e.g., into any tissue) administration. Transdermal delivery includes, but is not limited to, intradermal (e.g., into the dermis or epidermis), transdermal (e.g., percutaneous), and transmucosal administration (e.g., into or through skin or mucosal tissue). Intracavity administration includes, but is not limited to, administration into oral, vaginal, rectal, nasal, peritoneal, and intestinal cavities, as well as, intrathecal (e.g., into spinal canal), intraventricular (e.g., into the brain ventricles or the heart ventricles), intraatrial (e.g., into the heart atrium), and subarachnoid (e.g., into the subarachnoid spaces of the brain) administration.

In some embodiments, the invention includes compositions comprising a heterologous HN polypeptide produced from a microalgal host cell. In some embodiments, the composition comprises an aqueous liquid carrier. In further embodiments, the aqueous liquid carrier is a culture supernatant. In some embodiments, the compositions of the invention include conventional pharmaceutically acceptable excipients known in the art such as, but not limited to, human serum albumin, ion exchangers, alumina, lecithin, buffer substances such as phosphates, glycine, sorbic acid, potassium sorbate, and salts or electrolytes such as protamine sulfate, as well as excipients listed in, for example, *Remington: The Science and Practice of Pharmacy*, $21^{st}$ ed. (2005).

The most effective mode of administration and dosage regimen for the compositions of this invention depends upon the severity and course of the disease, the subject's health and response to treatment and the judgment of the treating physician. Accordingly, the dosages of the compositions should be titrated to the individual subject. Nevertheless, an effective dose of the compositions of this invention can be in the range of from 1 mg/kg to 2000 mg/kg, 1 mg/kg to 1500 mg/kg, 1 mg/kg to 1000 mg/kg, 1 mg/kg to 500 mg/kg, 1 mg/kg to 250 mg/kg, 1 mg/kg to 100 mg/kg, 1 mg/kg to 50 mg/kg, 1 mg/kg to 25 mg/kg, 1 mg/kg to 10 mg/kg, 500 mg/kg to 2000 mg/kg, 500 mg/kg to 1500 mg/kg, 500 mg/kg to 1000 mg/kg, 100 mg/kg to 2000 mg/kg, 100 mg/kg to 1500 mg/kg, 100 mg/kg to 1000 mg/kg, or 100 mg/kg to 500 mg/kg.

EXAMPLE 1

Construction of the pCL0081 Expression Vector

Figure 3:
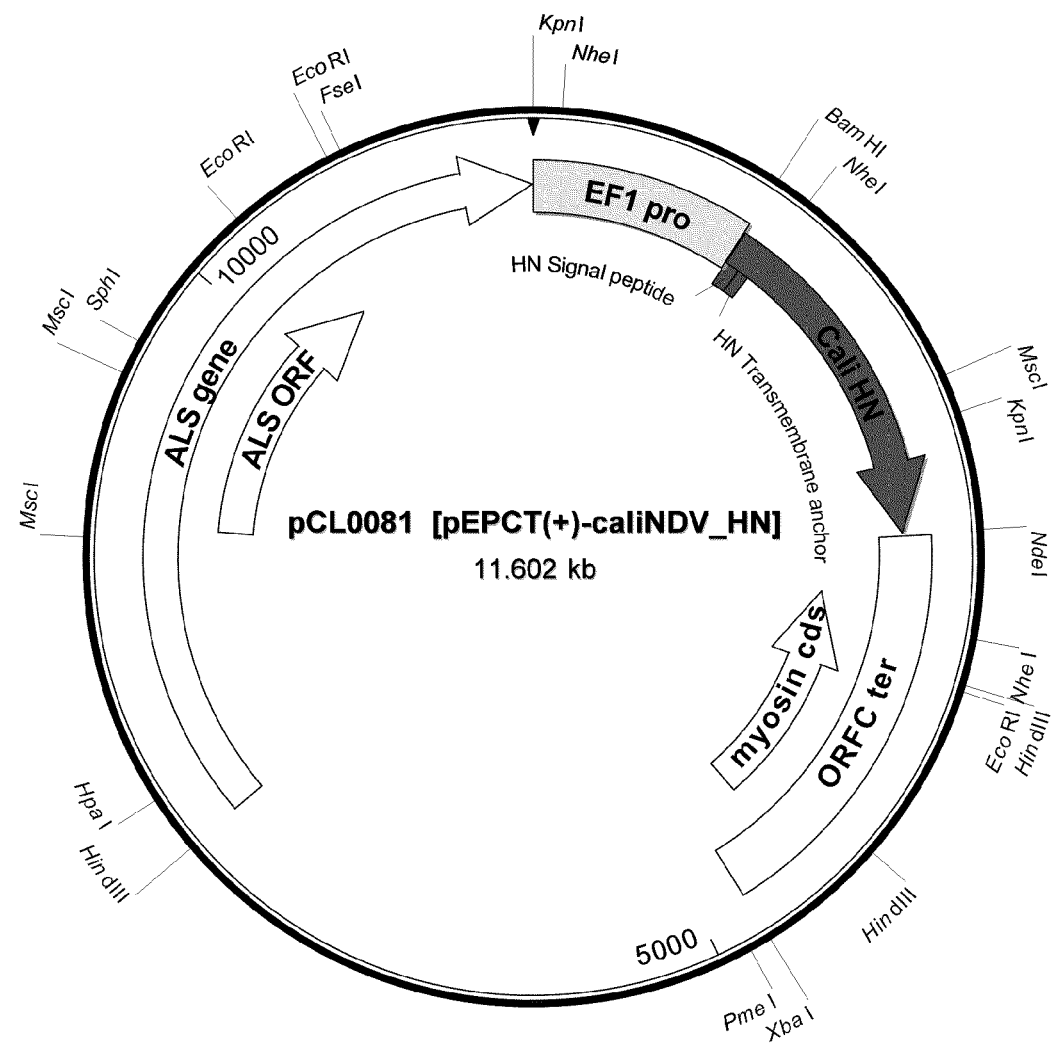

The vector pAB0018 (ATCC Accession No. PTA-9616) was digested with BamHI and NdeI resulting in two fragments of 838 base pairs (bp) and 9879 bp in length. The 9879 bp fragment was fractionated by standard electrophoretic techniques in an agar gel, purified using commercial DNA purification kits, and ligated to a synthetic sequence (SEQ ID NO: 1; see FIG. 1) that had also been previously digested with BamHI and NdeI. The ligation product was then used to transform commercially supplied strains of competent DH5-α E. coli cells (Invitrogen, CA) using the manufacturer's protocol. These plasmids were then screened by restriction digests or PCR to confirm that the ligation generated the expected plasmid structures. One such plasmid vector resulting from the procedure was verified by Sanger sequencing and designated pCL0081. See FIG. 3. The pCL0081 vector includes a promoter from the *Schizochytrium* elongation factor-1 gene (EF1) to drive expression of the HN transgene, the OrfC terminator (also known as the PFA3 terminator) following the HN transgene, and a selection marker cassette conferring resistance to sulfometuron methyl.

SEQ ID NO: 1 encodes the HN protein of Newcastle disease virus ("California strain"), also known as isolate gamefowl/U.S.(CA)/211472/02). The protein sequence matches that of GenBank Accession No. AAS67142. The specific nucleic acid sequence of SEQ ID NO: 1 was codon-optimized and synthesized for expression in *Schizochytrium* by Blue Heron Biotechnology (Bothell, Wash.) as guided by the *Schizochytrium* codon usage table shown in FIG. 2.

EXAMPLE 2

Expression and Characterization of HN Protein Produced in *Schizochytrium*

*Schizochytrium* sp. ATCC 20888 was used as a host cell for transformation with the pCL0081 vector.

Electroporation with enzyme pretreatment—Cells were grown in 50 mL of M50-20 media (see U.S. Publ. No. 2008/0022422) on a shaker at 200 rpm for 2 days at 30° C. The cells were diluted at 1:100 into M2B media (see following paragraph) and grown overnight (16-24 h), attempting to reach mid-log phase growth ($OD_{600}$ of 1.5-2.5). The cells were centrifuged in a 50 mL conical tube for 5 min at about 3000×g. The supernatant was removed and the cells were resuspended in 1 M mannitol, pH 5.5, in a suitable volume to reach a final concentration of 2 $OD_{600}$ units. 5 mL of cells were aliquoted into a 25 mL shaker flask and amended with 10 mM $CaCl_2$ (1.0 M stock, filter sterilized) and 0.25 mg/mL Protease XIV (10 mg/mL stock, filter sterilized; Sigma-Aldrich, St. Louis, Mo.). Flasks were incubated on a shaker at 30° C. and about 100 rpm for 4 h. Cells were monitored under the microscope to determine the degree of protoplasting, with single cells desired. The cells were centrifuged for 5 min at about 2500×g in round-bottom tubes (i.e., 14 mL Falcon™ tubes, BD Biosciences, San Jose, Calif.). The supernatant was removed and the cells were gently resuspended with 5 mL of ice cold 10% glycerol. The cells were re-centrifuged for 5 min at about 2500×g in round-bottom tubes. The supernatant was removed and the cells were gently resuspended with 500 μL of ice cold 10% glycerol, using wide-bore pipette tips. 90 μL of cells were aliquoted into a prechilled electro-cuvette (Gene Pulser® cuvette-0.2 cm gap, Bio-Rad, Hercules, Calif.). 1 μg to 5 μg of DNA (in less than or equal to a 10 μL volume) was added to the cuvette, mixed gently with a pipette tip, and placed on ice for 5 min. Cells were electroporated at 200 ohms (resistance), 25 μF (capacitance), and 500V. 0.5 mL of M50-20 media was added immediately to the cuvette. The cells were then transferred to 4.5 mL of M50-20 media in a 25 mL shaker flask and incubated for 2-3 h at 30° C. and about 100 rpm on a shaker. The cells were centrifuged for 5 min at about 2500×g in round bottom tubes. The supernatant was removed and the cell pellet was resuspended in 0.5 mL of M50-20 media. Cells were plated onto an appropriate number (2 to 5) of M2B plates with appropriate selection (if needed) and incubated at 30° C.

M2B media consisted of 10 g/L glucose, 0.8 g/L (NH4)2SO4, 5 g/L Na2SO4, 2 g/L MgSO4.7H2O, 0.5 g/L KH2PO4, 0.5 g/L KCl, 0.1 g/L CaCl2.2H2O, 0.1 M MES (pH 6.0), 0.1% PB26 metals, and 0.1% PB26 Vitamins (v/v). PB26 vitamins consisted of 50 mg/mL vitamin B12, 100 μg/mL thiamine, and 100 μg/mL Ca-pantothenate. PB26 metals were adjusted to pH 4.5 and consisted of 3 g/L FeSO4.7H2O, 1 g/L MnCl2.4H2O, 800 mg/mL ZnSO4.7H2O, 20 mg/mL CoCl2.6H2O, 10 mg/mL Na2MoO4.2H2O, 600 mg/mL CuSO4.5H2O, and 800 mg/mL NiSO4.6H2O. PB26 stock solutions were filter-sterilized separately and added to the broth after autoclaving. Glucose, KH2PO4, and CaCl2.2H2O were each autoclaved separately from the remainder of the broth ingredients before mixing to prevent salt precipitation and carbohydrate caramelizing. All medium ingredients were purchased from Sigma Chemical (St. Louis, Mo.).

Cryostocks of transgenic *Schizochytrium* (transformed with pCL0081) were grown in M50-20 to confluence and then propagated in 50 mL baffled shake flasks at 27° C., 200 rpm for 48 hours (h) in a medium containing the following (per liter):

| | |
|---|---|
| $Na_2SO_4$ | 13.62 g |
| $K_2SO_4$ | 0.72 g |
| KCl | 0.56 g |
| $MgSO_4 \cdot 7H_2O$ | 2.27 g |
| $(NH_4)2SO_4$ | 3 g |
| $CaCl_2 \cdot 2H_2O$ | 0.19 g |
| MSG monohydrate | 3 g |
| MES | 21.4 g |
| $KH_2PO_4$ | 0.4 g |

The volume was brought to 900 mL with deionized $H_2O$ and the pH was adjusted to 6 before autoclaving for 35 min. Filter-sterilized glucose (50 g/L), vitamins (2 mL/L) and trace metals (2 mL/L) were then added to the medium and the volume was adjusted to one liter. The vitamin solution contained 0.16 g/L vitamin B12, 9.75 g/L thiamine, and 3.33 g/L Ca-pentothenate. The trace metal solution (pH 2.5) contained 1.00 g/L citric acid, 5.15 g/L $FeSO_4.7H_2O$, 1.55 g/L $MnCl_2.4H_2O$, 1.55 g/L $ZnSO_4.7H_2O$, 0.02 g/L $CoCl_2.6H_2O$, 0.02 g/L $Na_2MoO_4.2H_2O$, 1.035 g/L $CuSO_4.5H_2O$, and 1.035 g/L $NiSO_4.6H_2O$.

Figure 4:
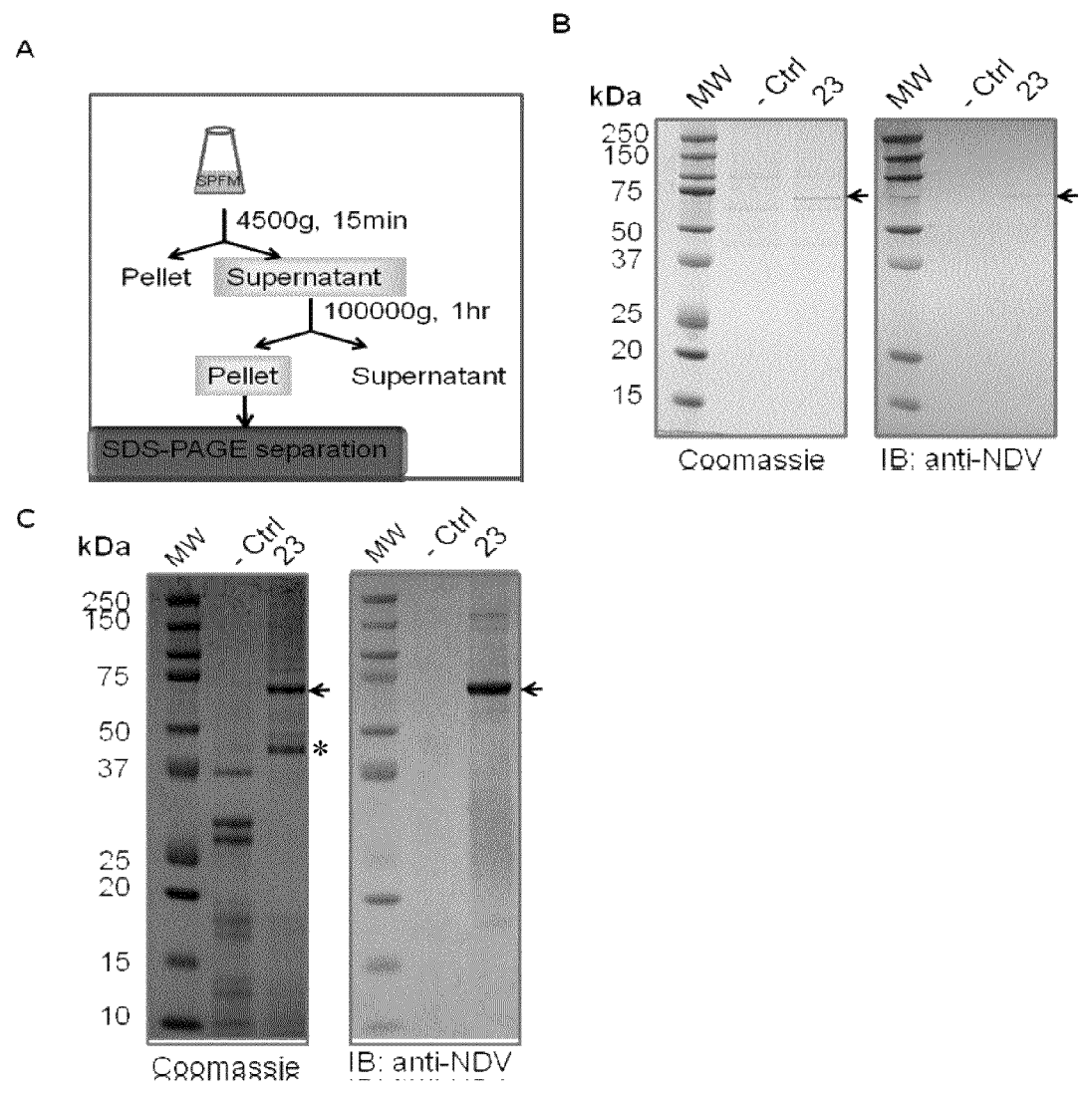

*Schizochytrium* cultures were transferred to 50 mL conical tubes and centrifugated at 3000×g or 4500×g for 15 min. See FIG. 4A. The supernatant resulting from this centrifugation, termed the "cell-free supernatant," was used for a hemagglutination activity assay.

The cell-free supernatant was further ultracentrifugated at 100,000×g for 1 h. See FIG. 4A. The resulting pellet of the insoluble fraction containing the HN protein was resuspended in phosphate buffer saline (PBS) and used for peptide sequence analysis as well as glycosylation analysis.

The expression of the HN protein from transgenic *Schizochytrium* CL0081-23 ("23") was verified by immunoblot analysis following standard immunoblotting procedure. The proteins from the cell-free supernatant and from the pelleted insoluble fraction were separated by sodium dodecyl sulfate-polyacrylamide gel electrophoresis (SDS-PAGE) on a 4-12% bis-tris gel (Invitrogen). The proteins were then stained with Coomassie blue (SimplyBlue Safe Stain, Invitrogen) or transferred onto polyvinylidene fluoride membrane and probed for the presence of HN protein with anti-Newcastle Disease Virus (NDV) antiserum from chicken (1:1000 dilution, Charles River Laboratories) followed by anti-chicken secondary antibody coupled to alkaline phosphatase (1:5000 dilution, AP-AffiniPure Goat Anti-Chicken #103-055-155, Jackson ImmunoResearch Laboratories, Inc.). The membrane was then treated with 5-bromo-4-chloro-3-indoyl-phosphate/nitroblue tetrazolium solution (BCIP/NBT) according to the manufacturer's instructions (KPL, Gaithersburg, Md.). Coomassie blue-stained gels and corresponding anti-NDV immunoblots for the transgenic *Schizochytrium* "CL0081-23" are shown in FIG. 4B and FIG. 4C. The recombinant HN protein was detected in the cell-free supernatant (FIG. 4B) and in the insoluble fraction (FIG. 4C). The negative control (−Ctrl) was the wild-type strain of *Schizochytrium* sp. ATCC 20888 or the transgenic *Schizochytrium* AB0018. In addition, the pelleted insoluble fraction was lysed, centrifuged twice at 4500×g for 10 min, and HN protein was detected in the supernatant (termed the "cell-free extract") from transgenic *Schizochytrium* expressing the HN protein (data not shown).

The insoluble fraction resulting from 100,000×g centrifugation of the cell-free supernatant was separated by SDS-PAGE and stained with Coomassie blue or transferred to PVDF and immunoblotted with anti-NDV antiserum from chicken, as described above. The band corresponding to the cross-reaction in immunoblot was excised from the Coomassie-stained gel and peptide sequence analysis was performed. Briefly, the bands of interest were washed/destained in 50% ethanol, 5% acetic acid. The gel pieces were then dehydrated in acetonitrile, dried in a SpeedVac® (Thermo Fisher Scientific, Inc., Waltham, Mass.), and digested with trypsin by adding 5 μL of 10 ng/μL trypsin in 50 mM ammonium bicarbonate and incubating overnight at room temperature. The peptides that were formed were extracted from the polyacrylamide in two aliquots of 30 μL 50% acetonitrile with 5% formic acid. These extracts were combined and evaporated to <10 μL in a SpeedVac® and then resuspended in 1% acetic acid to make up a final volume of approximately 30 μL for LC-MS analysis. The LC-MS system was a Finnigan™ LTQ™ Linear Ion Trap Mass Spectrometer (Thermo Electron Corporation, Waltham, Mass.). The HPLC column was a self-packed 9 cm×75 μm Phenomenex Jupiter™ C18 reversed-phase capillary chromatography column (Phenomenex, Torrance, Calif.). Then, μL volumes of the extract were injected and the peptides were eluted from the column by an acetonitrile/0.1% formic acid gradient at a flow rate of 0.25 μL/min and were introduced into the source of the mass spectrometer on-line. The microelectrospray ion source was operated at 2.5 kV. The digest was analyzed using a selective reaction (SRM) experiment in which the mass spectrometer fragments a series of m/z ratios over the entire course of the LC experiment. The fragmentation pattern of the peptides of interest was then used to produce chromatograms. The peak areas for each peptide was determined and normalized to an internal standard. The internal standards used in this analysis were proteins that have an unchanging abundance between the samples being studied. The final comparison between the two systems was determined by comparing the normalized peak ratios for each protein. The collision-induced dissociation spectra were then searched against the NCBI database. The HN protein was identified by a total of 32 peptides covering 68% of the protein sequence. The specific peptides that were sequenced are shown in FIG. 5.

The presence of glycans on the HN protein was first evaluated by enzymatic treatment. The insoluble fraction of the transgenic *Schizochytrium* "CL0081-23" was resuspended in PBS and digested with EndoH or PNGase F according to manufacturer's instructions (New England Biolabs, Ipswich, Mass.). Removal of glycans was then identified by the expected shift in mobility when separating the proteins on 12% SDS-PAGE stained with Coomassie blue (FIG. 6A) or by immunoblotting with anti-NDV antiserum (FIG. 6B). The negative control ("−Ctrl") for immunoblotting was the transgenic *Schizochytrium* AB0018. The negative control for the enzymatic treatment was the transgenic *Schizochytrium* "CL0081-23" incubated without enzymes ("NT"=non-treated).

The glycosylation profile of the HN protein produced in *Schizochytrium* was analyzed by matrix-assisted laser-desorption ionization time-of-flight mass spectrometry and nanospray ionization-linear ion trap mass spectrometry. Briefly, Coomassie blue stained gel slices of the proteins of interest were cut into smaller pieces (~1 $mm^3$) and destained alternately with 40 mM ammonium bicarbonate (AmBic) and 100% acetonitrile until the color turned clear. The destained gel was reswelled in 10 mM DTT in 40 mM Ambic at 55° C. for 1 h. The DTT solution was exchanged with 55 mM iodoacetamide (IAM) and incubated in the dark for 45 min. Incubation was followed by washing alternately with 40 mM AmBic and 100% acetonitrile twice. The dehydrated gel was reswelled with trypsin solution (trypsin in 40 mM AmBic) on ice for 45 min initially, and protein digestion was carried out at 37° C. overnight. The supernatant was transferred into another tube. Peptides and glycopeptides were extracted from the gel in series with 20% acetonitrile in 5% formic acid, 50% acetonitrile in 5% formic acid, and then 80% acetonitrile in 5% formic acid. The sample solutions were dried and combined into one tube. Extracted tryptic digest was passed through a C18 Sep-Pak® cartridge (Waters Corporation, Milford, Mass.) and washed with 5% acetic acid to remove contaminants (such as salts and SDS). Peptides and glycopeptides were eluted in series with 20% iso-propanol in 5% acetic acid, 40% iso-propanol in 5% acetic acid, and 100% iso-propanol, and then dried in a speed vacuum concentrator. The dried samples were combined and reconstituted with 50 mM sodium phosphate buffer (pH 7.5) and heated at 100° C. for 5 min to inactivate trypsin. The tryptic digest was incubated with PNGase F at 37° C. overnight to release N-glycans. After digestion, the sample was passed through a C18 Sep-Pak® cartridge and the carbohydrate fraction was eluted with 5% acetic acid and dried by lyophilization. Released N-linked oligosaccharides were permethylated based on the method of Anumula, K. R., and Taylor, P. B. *Anal. Biochem.* 203(1): 101-108 (1992) and profiled by mass spectrometry (MS).

Mass spectrometric analysis was performed following the method developed at the Complex Carbohydrates Research Center (Aoki, K. et al., *J. Biol. Chem.* 23: 282:9127-9142 (2007)). Mass analysis was determined by using NSI-LTQ/$MS_n$. Briefly, permethylated glycans were dissolved in 1 mM NaOH in 50% methanol and infused directly into the instrument (Finnigan™ LTQ™ Linear Ion Trap Mass Spectrometer) at a constant flow rate of 0.4 μL/min. The MS analysis was performed in the positive ion mode.

Total ion mapping was performed to examine the presence of fragment ions indicative of glycans. For total ion mapping, automated MS/MS analysis (at 35 collision energy), m/z range from 500 to 2000 was scanned in successive 2.8 mass unit windows that overlapped the preceding window by 2 mass units. All MS/MS data from m/z 500 through m/z 2000 were taken and then the raw data were analyzed manually.

Figure 7:
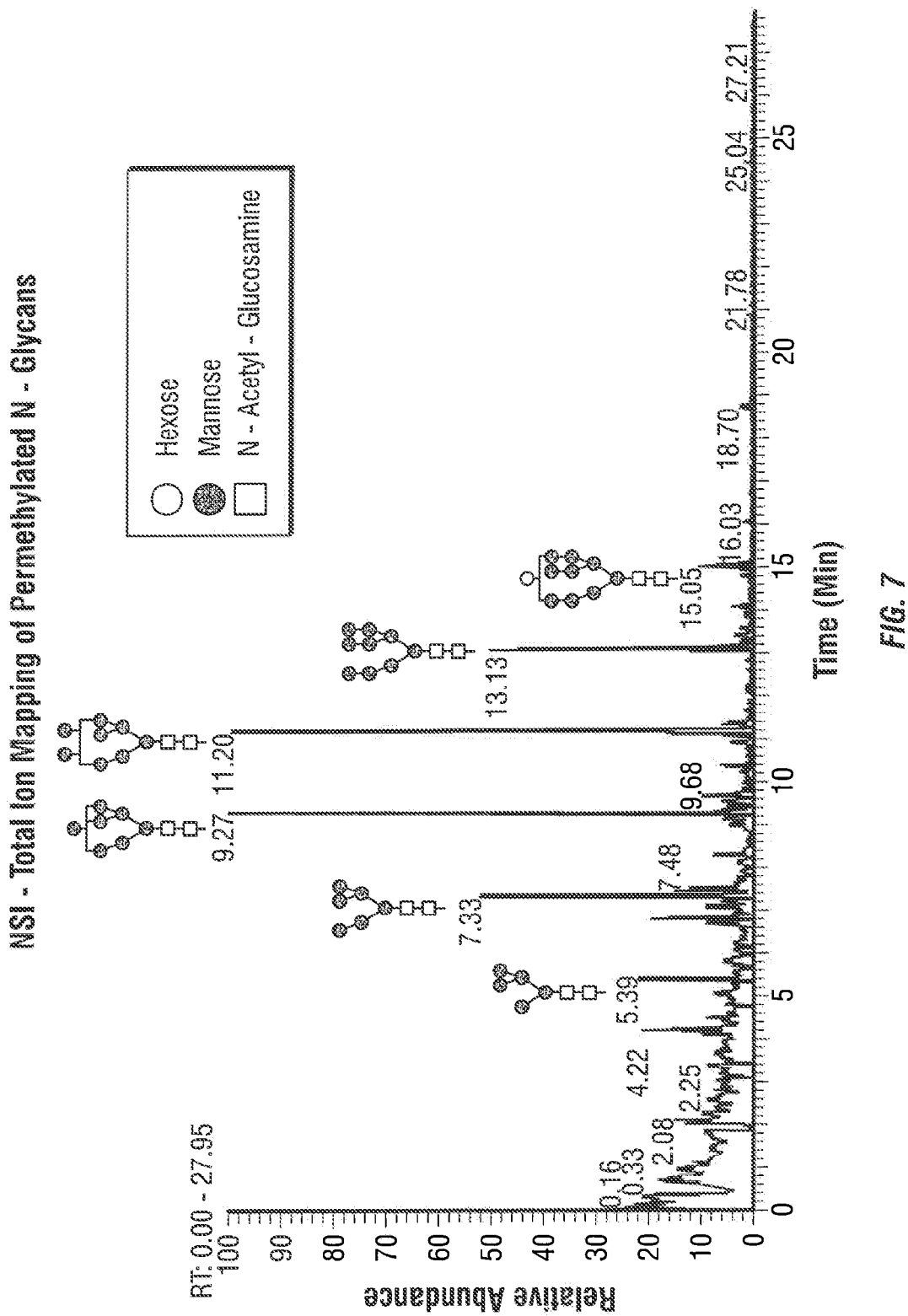

The chromatogram and table of glycan species obtained by NSI-total ion mapping are shown in FIG. 7 and FIG. 8, respectively. The chromatogram was processed by the scan filter; a neutral loss of m/z 139, is characteristic of high-mannose type glycans. Total ion mapping revealed that this sample contains a series of high-mannose type glycans with long mannose chains. These results are similar to the N-glycan structures detected on native *Schizochytrium* secreted proteins and heterologously expressed proteins, as determined by the same methodology (data not shown).

The activity of the HN protein produced in *Schizochytrium* was evaluated by a hemagglutination activity assay. The functional HN protein displays an hemagglutination activity that is readily detected by a standard hemagglutination activity assay. Briefly, 50 µL of doubling dilutions of low speed supernatant in PBS were prepared in a 96-well microtiter plate. Equal volume of an approximate 1% solution of turkey red blood cells (Fitzgerald Industries) in PBS was then added to each well followed by incubation at room temperature for 30 min. The degree of agglutination was then analyzed visually. The hemagglutination activity unit (HAU) is defined as the highest dilution of cell-free supernatant that causes visible hemagglutination in the well.

Figure 9:
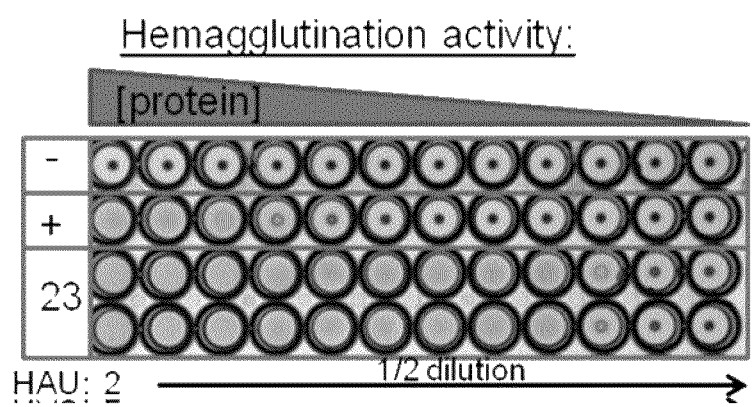

Typical activity was found to be in the order of 512 HAU in transgenic *Schizochytrium* "CL0081-23" supernatant (FIG. 9). PBS or the wild-type strain of *Schizochytrium* sp. ATCC 20888, grown and prepared in the same manner as the transgenic strains, were used as the negative control and did not show any hemagglutination activity. The Influenza Hemagglutinin (HA) recombinant protein (Protein Sciences #3006 H5N1, dilution 1:1000 in PBS) was used as a positive control. The hemagglutination activity of HN from transgenic *Schizochytrium* CL0081-23 supernatant was found to be stable through multiple rounds of freeze/thawing and was preserved after 2 µM filtration.

EXAMPLE 3

Expression and Characterization of Parainfluenza HN Protein Produced in *Schizochytrium*

*Schizochytrium* sp. ATCC 20888 is used as a host cell for transformation with a vector comprising a sequence that encodes the parainfluenza HN protein. A representative sequence for the parainfluenza HN protein is provided as SEQ ID NO: 11 (Human parainfluenza 3 virus (strain NIH 47885) from GenBank Accession No. P08492). Some cells are transformed with a vector comprising a sequence encoding the native signal anchor sequence associated with the parainfluenza HN protein. Other cells are transformed with a vector comprising a sequence encoding a different signal anchor sequence, including a *Schizochytrium* signal anchor sequence, that is fused to the sequence encoding the parainfluenza HN protein, such that the parainfluenza HN protein is expressed with a heterologous signal anchor sequence. Transformation is performed, and cryostocks are grown and propagated as described in Example 2. *Schizochytrium* cultures are transferred to 50 mL conical tubes and centrifuged at 3000×g or 4500×g for 15 min to yield a low-speed supernatant. The low-speed supernatant is further ultracentrifuged at 100,000×g for 1 h. See FIG. 4A. The resulting pellet of the insoluble fraction containing the parainfluenza HN protein is resuspended in phosphate buffer saline (PBS) and used for peptide sequence analysis as well as glycosylation analysis as described in Example 2.

The expression of the parainfluenza HN protein from transgenic *Schizochytrium* is verified by immunoblot analysis following standard immunoblotting procedure as described in Example 2, using anti-parainfluenza HN antiserum and a secondary antibody at appropriate dilutions. The recombinant parainfluenza HN protein is detected in the low-speed supernatant and the insoluble fraction. Additionally, the recombinant parainfluenza HN protein is detected in cell-free extracts from transgenic *Schizochytrium* expressing the parainfluenza HN protein.

The activity of the parainfluenza HN protein produced in *Schizochytrium* is evaluated by a parainfluenza HN activity assay. A functional parainfluenza HN protein displays an parainfluenza HN activity that is readily detected by a standard parainfluenza HN activity assay.

All of the various aspects, embodiments, and options described herein can be combined in any and all variations.

What is claimed is:

1. A method for production of a hemagglutinin-neuraminidase (HN) polypeptide, wherein said HN polypeptide is glycosylated and comprises full length HN polypeptide, a membrane domain and a native HN signal peptide, said method comprising culturing a recombinant microalgal host cell in a medium, wherein the recombinant microalgal host cell comprises a heterologous nucleic acid molecule comprising the sequence of SEQ ID NO:1 encoding the HN polypeptide to produce the HN polypeptide, and wherein the microalgal host cell is free of polynucleotide sequences encoding other heterologous viral polypeptides, whereby the HN polypeptide is secreted into the medium by action of the signal peptide, and recovering the HN polypeptide from the medium.

2. The method of claim 1, wherein the HN polypeptide is at least 90% identical to SEQ ID NO:2.

3. A method of producing a composition comprising a heterologous HN polypeptide, the method comprising:

(a) expressing a heterologous HN polypeptide encoded by a polynucleotide comprising the sequence of SEQ ID NO:1 in a microalgal host cell, wherein said HN polypeptide is glycosylated and comprises full length HN polypeptide, a membrane domain and a native HN signal peptide, and (b) culturing the microalgal host cell under conditions sufficient to produce the heterologous FN polypeptide wherein the composition is produced as the culture supernatant comprising the heterologous FN polypeptide, and wherein the microalgal host cell is free of polynucleotide sequences encoding other heterologous viral polypeptides.

4. The method of claim 3, further comprising removing the culture supernatant from the composition and resuspending the heterologous HN polypeptide in an aqueous liquid carrier.

5. The method of claim 1 or claim 3, wherein the host cell is a Labyrinthulomycota host cell.

6. The method of claim 5, wherein the host cell is a *Schizochytrium* or a *Thraustochytrium* host cell.

7. A recombinant microalgal cell expressing an HN polypeptide, wherein said HN polypeptide is glycosylated and comprises full length HN polypeptide, a membrane domain and a native HN signal peptide, comprising a nucleic acid molecule comprising a polynucleotide sequence of SEQ ID NO:1 that encodes the HN protein, wherein the microalgal cell is free of polynucleotide sequence encoding other heterologous viral proteins.

8. The microalgal cell of claim 7, wherein the HN protein is at least 90% sequence identical to SEQ ID NO:2.

9. The microalgal cell of claim 7, wherein the microalgal cell is a Labyrinthulomycota cell.

10. The microalgal cell of claim 9, wherein the microalgal cell is a *Schizochytrium* or a *Thraustochytrium cell.*

11. The method of claim 2, wherein the HN polypeptide has the sequence of SEQ ID NO:2.

12. The microalgal cell of claim 8, wherein the HN protein has the sequence of SEQ ID NO:2.

* * * * *

SEQUENCE LISTING

```
<160> NUMBER OF SEQ ID NOS: 11

<210> SEQ ID NO 1
<211> LENGTH: 1728
<212> TYPE: DNA
<213> ORGANISM: Artificial Sequence
<220> FEATURE:
<223> OTHER INFORMATION: Codon optimized HN

<400> SEQUENCE: 1
ggatccatgg accgtgtcgt ctcccgcgtg gtcctcgaga acgaggagcg tgaggccaag      60
aacacctggc gccttgtctt tcgtgtcgcc gtcctctccc ttattgtcat gaccctcgcc     120
atctccgtcg ccgccctcgt ctacagcatg gaggctagca ccccaacga tctcgccgga     180 atctcgactg ttatctcccg cgccgaggac cgcgtcacct ccctcctcaa ctccaaccag     240
gatgtcgttg atcgcgtcta caagcaggtc gccctcgagt cccctctcgc cctccttaac     300
accgagagca tcattatgaa cgccattacc tccctcagct accagattaa cggcgccgcc     360
```

-continued

```
aactcgtccg gctgcggcgc ccccgtccat gaccctgatt acatcggcgg cgtcggcaag    420
gagctcatcg tcgacgacac tagcgatgcc acgtccttct accctagcgc ctaccaggag    480
cacctcaact tcatccctgc ccccactacc ggctccggct gcacccgcat tcccagcttc    540
gacatgtccg ccactcacta ctgctacacc ataacgtca tcctttcggg ttgccgcgac     600
cactcccaca gccaccagta cctcgccctc ggagttcttc gtacgtccgc caccggccgc    660 gtctttttt ccaccctccg cagcatcaac ctcgacgata cccagaaccg caagagctgc     720
tcggtctccg ccaccccgct cggctgcgac atgctctgct ccaaggtcac cgagacggag    780
gaggaggatt acaagtccgt taccccact tcgatggtcc acggccgcct tggcttcgac     840
ggccagtacc acgagaagga cctcgacgtc accgttctct taaggactg ggttgccaac     900 taccccggcg tcggcggcgg ctccctcatc gatgaccgcg tctggtttcc tgtctacggt    960
ggtctcaagc taacagccc ctccgatacc gcccaggagg taagtacgt gatctacaag     1020 cgctacaaca cacctgccc tgacgagcag gattaccagg tccgcatggc caagtcctcg    1080
tacaagcccg gtcgtttcgg cggcaagcgc gtccagcagg ccattctctc gatcaaggtc    1140
tcgaccagcc tcggagagga ccccgtgctc accgttcccc ctaacaccgt cacccttatg    1200
ggcgccgagg gccgcatcct caccgtcggt acctcccact tcctctacca gcgcggctcg    1260
agctactttt cccctgccct tctttacccc atgactgttc gcaacaagac tgctaccctc    1320
cacagcccct acacctttaa cgccttcacg cgccccggaa gcgtcccctg ccaggcgagc    1380
gcccgctgcc ctaactcctg cattaccggc gtctacaccg accttaccc tgtcgtcttt    1440 caccgcaacc atacccttcg cggcgtcttc ggtactatgc ttgataacga gcaggcccgc    1500
ctcaaccccg tctccgccat tttcgactac acttcccgct cccgtatcac ccgcgtctcc    1560
tccacctcca ccaaggccgc ctacaccacc tccacctgct ttaaggttgt caagactaac    1620
aaggtctact gcctctccat cgccgagatt agcaacaccc tcttcggaga gttccgcatt    1680 gtcccctgc tcgtcgagat cctcaaggac gatcgcgttt aacatatg                  1728
```

<210> SEQ ID NO 2
<211> LENGTH: 571
<212> TYPE: PRT
<213> ORGANISM: Artificial Sequence
<220> FEATURE:
<223> OTHER INFORMATION: Codon optimized HN

<400> SEQUENCE: 2

```
Met Asp Arg Val Val Ser Arg Val Val Leu Glu Asn Glu Glu Arg Glu
1               5                   10                  15

Ala Lys Asn Thr Trp Arg Leu Val Phe Arg Val Ala Val Leu Ser Leu
            20                  25                  30

Ile Val Met Thr Leu Ala Ile Ser Val Ala Ala Leu Val Tyr Ser Met
        35                  40                  45

Glu Ala Ser Thr Pro Asn Asp Leu Ala Gly Ile Ser Thr Val Ile Ser
    50                  55                  60

Arg Ala Glu Asp Arg Val Thr Ser Leu Leu Asn Ser Asn Gln Asp Val
65                  70                  75                  80

Val Asp Arg Val Tyr Lys Gln Val Ala Leu Glu Ser Pro Leu Ala Leu
                85                  90                  95

Leu Asn Thr Glu Ser Ile Ile Met Asn Ala Ile Thr Ser Leu Ser Tyr
            100                 105                 110

Gln Ile Asn Gly Ala Ala Asn Ser Ser Gly Cys Gly Ala Pro Val His
```

```
            115                 120                 125
Asp Pro Asp Tyr Ile Gly Gly Val Gly Lys Glu Leu Ile Val Asp Asp
            130                 135                 140

Thr Ser Asp Ala Thr Ser Phe Tyr Pro Ser Ala Tyr Gln Glu His Leu
145                 150                 155                 160

Asn Phe Ile Pro Ala Pro Thr Thr Gly Ser Gly Cys Thr Arg Ile Pro
            165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
            195                 200                 205

Gly Val Leu Arg Thr Ser Ala Thr Gly Arg Val Phe Phe Ser Thr Leu
            210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
            245                 250                 255

Thr Glu Glu Glu Asp Tyr Lys Ser Val Thr Pro Thr Ser Met Val His
            260                 265                 270

Gly Arg Leu Gly Phe Asp Gly Gln Tyr His Glu Lys Asp Leu Asp Val
            275                 280                 285

Thr Val Leu Phe Lys Asp Trp Val Ala Asn Tyr Pro Gly Val Gly Gly
            290                 295                 300

Gly Ser Leu Ile Asp Asp Arg Val Trp Phe Pro Val Tyr Gly Gly Leu
305                 310                 315                 320

Lys Pro Asn Ser Pro Ser Asp Thr Ala Gln Glu Gly Lys Tyr Val Ile
            325                 330                 335

Tyr Lys Arg Tyr Asn Asn Thr Cys Pro Asp Glu Gln Asp Tyr Gln Val
            340                 345                 350

Arg Met Ala Lys Ser Ser Tyr Lys Pro Gly Arg Phe Gly Gly Lys Arg
            355                 360                 365

Val Gln Gln Ala Ile Leu Ser Ile Lys Val Ser Thr Ser Leu Gly Glu
            370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
            405                 410                 415

Gly Ser Ser Tyr Phe Ser Pro Ala Leu Leu Tyr Pro Met Thr Val Arg
            420                 425                 430

Asn Lys Thr Ala Thr Leu His Ser Pro Tyr Thr Phe Asn Ala Phe Thr
            435                 440                 445

Arg Pro Gly Ser Val Pro Cys Gln Ala Ser Ala Arg Cys Pro Asn Ser
            450                 455                 460

Cys Ile Thr Gly Val Tyr Thr Asp Pro Tyr Pro Val Val Phe His Arg
465                 470                 475                 480

Asn His Thr Leu Arg Gly Val Phe Gly Thr Met Leu Asp Asn Glu Gln
            485                 490                 495

Ala Arg Leu Asn Pro Val Ser Ala Ile Phe Asp Tyr Thr Ser Arg Ser
            500                 505                 510

Arg Ile Thr Arg Val Ser Ser Thr Ser Thr Lys Ala Ala Tyr Thr Thr
            515                 520                 525

Ser Thr Cys Phe Lys Val Val Lys Thr Asn Lys Val Tyr Cys Leu Ser
            530                 535                 540
```

```
Ile Ala Glu Ile Ser Asn Thr Leu Phe Gly Glu Phe Arg Ile Val Pro
545                 550                 555                 560

Leu Leu Val Glu Ile Leu Lys Asp Asp Arg Val
                565                 570

<210> SEQ ID NO 3
<211> LENGTH: 51
<212> TYPE: PRT
<213> ORGANISM: Schizochytrium sp. ATCC 20888
<220> FEATURE:
<223> OTHER INFORMATION: GlcNac-transferase-I-like protein

<400> SEQUENCE: 3

Met Arg Gly Pro Gly Met Val Gly Leu Ser Arg Val Asp Arg Glu His
1               5                   10                  15

Leu Arg Arg Arg Gln Gln Gln Ala Ala Ser Glu Trp Arg Arg Trp Gly
            20                  25                  30

Phe Phe Val Ala Thr Ala Val Val Leu Leu Val Phe Leu Thr Val Tyr
        35                  40                  45

Pro Asn Val
    50

<210> SEQ ID NO 4
<211> LENGTH: 153
<212> TYPE: DNA
<213> ORGANISM: Schizochytrium sp. ATCC 20888
<220> FEATURE:
<223> OTHER INFORMATION: signal anchor sequence

<400> SEQUENCE: 4
atgcgcggcc cgggcatggt cggcctcagc cgcgtggacc gcgagcacct gcggcggcgg      60
cagcagcagg cggcgagcga atggcggcgc tgggggttct cgtcgcgac ggccgtcgtc      120 ctgctcgtct ttctcaccgt atacccgaac gta                                  153

<210> SEQ ID NO 5
<211> LENGTH: 66
<212> TYPE: PRT
<213> ORGANISM: Schizochytrium sp. ATCC 20888
<220> FEATURE:
<223> OTHER INFORMATION: beta-1,2- xylosyltransferase-like protein

<400> SEQUENCE: 5

Met Arg Thr Arg Gly Ala Ala Tyr Val Arg Pro Gly Gln His Glu Ala
1               5                   10                  15

Lys Ala Leu Ser Ser Arg Ser Ser Asp Glu Gly Tyr Thr Thr Val Asn
            20                  25                  30

Val Val Arg Thr Lys Arg Lys Arg Thr Thr Val Ala Ala Leu Val Ala
        35                  40                  45

Ala Ala Leu Leu Val Thr Gly Phe Ile Val Val Val Phe Val Val
    50                  55                  60

Val Val
65

<210> SEQ ID NO 6
<211> LENGTH: 198
<212> TYPE: DNA
<213> ORGANISM: Schizochytrium sp. ATCC 20888
<220> FEATURE:
<223> OTHER INFORMATION: signal anchor sequence

<400> SEQUENCE: 6
```

```
atgcgcacgc ggggcgcggc gtacgtgcgg ccgggacagc acgaggcgaa ggcgctctcg    60
tcaaggagca gcgacgaggg atatacgacg gtcaacgttg tcaggaccaa gcgaaagagg   120
accactgtag ccgcgcttgt agccgcggcg ctgctggtga cgggctttat cgtcgtcgtc   180
gtcttcgtcg tcgttgtt                                                 198
```

<210> SEQ ID NO 7
<211> LENGTH: 64
<212> TYPE: PRT
<213> ORGANISM: Schizochytrium sp. ATCC 20888
<220> FEATURE:
<223> OTHER INFORMATION: beta-1,4-xylosidase-like protein

<400> SEQUENCE: 7

```
Met Glu Ala Leu Arg Glu Pro Leu Ala Ala Pro Pro Thr Ser Ala Arg
1               5                   10                  15

Ser Ser Val Pro Ala Pro Leu Ala Lys Glu Glu Gly Glu Glu Glu Asp
                20                  25                  30

Gly Glu Lys Gly Thr Phe Gly Ala Gly Val Leu Gly Val Ala Val
        35                  40                  45

Leu Val Ile Val Val Phe Ala Ile Val Ala Gly Gly Gly Asp Ile
    50                  55                  60
```

<210> SEQ ID NO 8
<211> LENGTH: 192
<212> TYPE: DNA
<213> ORGANISM: Schizochytrium sp. ATCC 20888
<220> FEATURE:
<223> OTHER INFORMATION: signal anchor sequence

<400> SEQUENCE: 8

```
atggaggccc tgcgcgagcc cttggctgcg ccgccaacgt cggcgcgatc gtcggtgcca    60
gcgccgctcg cgaaggagga gggggaggag gaggacgggg aaaaagggac gtttggggcg   120
ggggtcctcg gtgtcgtggc ggtgctcgtc atcgtggtgt ttgcgatcgt ggcgggaggc   180
ggaggcgata tt                                                      192
```

<210> SEQ ID NO 9
<211> LENGTH: 73
<212> TYPE: PRT
<213> ORGANISM: Schizochytrium sp. ATCC 20888
<220> FEATURE:
<223> OTHER INFORMATION: galactosyltransferase-like protein

<400> SEQUENCE: 9

```
Met Leu Ser Val Ala Gln Val Ala Gly Ser Ala His Ser Arg Pro Arg
1               5                   10                  15

Arg Gly Gly Glu Arg Met Gln Asp Val Leu Ala Leu Glu Glu Ser Ser
                20                  25                  30

Arg Asp Arg Lys Arg Ala Thr Ala Arg Pro Gly Leu Tyr Arg Ala Leu
        35                  40                  45

Ala Ile Leu Gly Leu Pro Leu Ile Val Phe Ile Val Trp Gln Met Thr
    50                  55                  60

Ser Ser Leu Thr Thr Ala Pro Ser Ala
65                  70
```

<210> SEQ ID NO 10
<211> LENGTH: 219
<212> TYPE: DNA
<213> ORGANISM: Schizochytrium sp. ATCC 20888

<220> FEATURE:
<223> OTHER INFORMATION: signal anchor sequence

<400> SEQUENCE: 10

```
atgttgagcg tagcacaagt cgcggggtcg gcccactcgc ggccgagacg aggtggtgag      60
cggatgcaag acgtgctggc cctggaggaa agcagcagag atcgaaaacg agcaacagca     120
aggcccgggc tatatcgcgc acttgcgatt ctggggctgc cgctcatcgt attcatcgta     180
tggcaaatga ctagctccct cacgactgcc ccgagcgcc                            219
```

<210> SEQ ID NO 11
<211> LENGTH: 572
<212> TYPE: PRT
<213> ORGANISM: Human parainfluenza 3 Virus

<400> SEQUENCE: 11

```
Met Glu Tyr Trp Lys His Thr Asn His Gly Lys Asp Ala Gly Asn Glu
1               5                   10                  15

Leu Glu Thr Ser Met Ala Thr His Gly Asn Lys Ile Thr Asn Lys Ile
            20                  25                  30

Thr Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Val Asn Asn Glu Phe Met Glu Val Thr Glu Lys Ile
65                  70                  75                  80

Gln Met Ala Ser Asp Asn Ile Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Pro Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn His Asp Gly Ser Ile Ser Thr Thr Arg Phe
    290                 295                 300

Lys Asn Asn Asn Ile Ser Phe Asp Gln Pro Tyr Ala Ala Leu Tyr Pro
```

-continued

```
                305                 310                 315                 320
Ser Val Gly Pro Gly Ile Tyr Tyr Lys Gly Lys Ile Ile Phe Leu Gly
            325                 330                 335
Tyr Gly Gly Leu Glu His Pro Ile Asn Glu Asn Ala Ile Cys Asn Thr
            340                 345                 350
Thr Gly Cys Pro Gly Lys Thr Gln Arg Asp Cys Asn Gln Ala Ser His
            355                 360                 365
Ser Pro Trp Phe Ser Asp Arg Arg Met Val Asn Ser Ile Ile Val Val
        370                 375                 380
Asp Lys Gly Leu Asn Ser Ile Pro Lys Leu Lys Val Trp Thr Ile Ser
385                 390                 395                 400
Met Arg Gln Asn Tyr Trp Gly Ser Glu Gly Arg Leu Leu Leu Leu Gly
                405                 410                 415
Asn Lys Ile Tyr Ile Tyr Thr Arg Ser Thr Ser Trp His Ser Lys Leu
            420                 425                 430
Gln Leu Gly Ile Ile Asp Ile Thr Asp Tyr Ser Asp Ile Arg Ile Lys
            435                 440                 445
Trp Thr Trp His Asn Val Leu Ser Arg Pro Gly Asn Asn Glu Cys Pro
        450                 455                 460
Trp Gly His Ser Cys Pro Asp Gly Cys Ile Thr Gly Val Tyr Thr Asp
465                 470                 475                 480
Ala Tyr Pro Leu Asn Pro Thr Gly Ser Ile Val Ser Ser Val Ile Leu
            485                 490                 495
Asp Ser Gln Lys Ser Arg Val Asn Pro Val Ile Thr Tyr Ser Thr Ser
            500                 505                 510
Thr Glu Arg Val Asn Glu Leu Ala Ile Arg Asn Lys Thr Leu Ser Ala
        515                 520                 525
Gly Tyr Thr Thr Thr Ser Cys Ile Thr His Tyr Asn Lys Gly Tyr Cys
        530                 535                 540
Phe His Ile Val Glu Ile Asn His Lys Ser Leu Asp Thr Phe Gln Pro
545                 550                 555                 560
Met Leu Phe Lys Thr Glu Ile Pro Lys Ser Cys Ser
                565                 570
```